US011111504B2

(12) United States Patent
Brydges et al.

(10) Patent No.: US 11,111,504 B2
(45) Date of Patent: Sep. 7, 2021

(54) METHODS FOR SCARLESS INTRODUCTION OF TARGETED MODIFICATIONS INTO TARGETING VECTORS

(71) Applicant: Regeneron Pharmaceuticals, Inc., Tarrytown, NY (US)

(72) Inventors: Susannah Brydges, Scarsdale, NY (US); Jose F. Rojas, Newburgh, NY (US); Gregg S. Warshaw, Bayside, NY (US); Chia-Jen Siao, New York, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 16/838,621

(22) Filed: Apr. 2, 2020

(65) Prior Publication Data

US 2020/0318134 A1    Oct. 8, 2020

Related U.S. Application Data

(60) Provisional application No. 62/829,327, filed on Apr. 4, 2019.

(51) Int. Cl.
| | | |
|---|---|---|
| *C12N 15/85* | (2006.01) | |
| *C12N 9/22* | (2006.01) | |
| *C12N 15/10* | (2006.01) | |

(52) U.S. Cl.
CPC .............. *C12N 15/85* (2013.01); *C12N 9/22* (2013.01); *C12N 15/102* (2013.01); *C12N 2310/20* (2017.05)

(58) Field of Classification Search
CPC ...... C12N 15/85; C12N 9/22; C12N 2310/20; C12N 15/102
See application file for complete search history.

(56) References Cited

U.S. PATENT DOCUMENTS

| | | |
|---|---|---|
| 9,580,715 B2 | 2/2017 | Schoenherr et al. |
| 9,738,897 B2 | 8/2017 | Schoenherr et al. |
| 2004/0018626 A1 | 1/2004 | Murphy et al. |
| 2010/0035768 A1 | 2/2010 | Gibson et al. |
| 2013/0298265 A1 | 11/2013 | Cunnac et al. |
| 2015/0211058 A1 | 7/2015 | Carstens |
| 2015/0376628 A1 | 12/2015 | Schoenherr et al. |
| 2016/0053272 A1 | 2/2016 | Wurtzel et al. |
| 2016/0115486 A1 | 4/2016 | Schoenherr et al. |
| 2016/0186147 A1 | 6/2016 | Cady et al. |
| 2017/0198268 A1 | 7/2017 | Jacobson et al. |
| 2018/0002706 A1 | 1/2018 | Wang et al. |
| 2018/0002708 A1 | 1/2018 | Schoenherr et al. |
| 2018/0105806 A1 | 4/2018 | Voigt et al. |
| 2018/0362989 A1 | 12/2018 | Wang et al. |
| 2019/0330659 A1 | 10/2019 | DeLoache et al. |
| 2019/0359973 A1 | 11/2019 | Kmiec et al. |
| 2020/0181591 A1 | 6/2020 | Jacobson et al. |
| 2020/0208161 A1 | 7/2020 | Schoenherr et al. |

FOREIGN PATENT DOCUMENTS

| | | |
|---|---|---|
| EP | 3568470 A1 | 11/2019 |
| WO | WO 2009/103027 A2 | 8/2009 |
| WO | WO 2010/102257 A2 | 9/2010 |
| WO | WO 2013/142578 A1 | 9/2013 |
| WO | WO 2014/089290 A1 | 6/2014 |
| WO | WO 2014/093622 A2 | 6/2014 |
| WO | WO 2015/200334 A1 | 12/2015 |
| WO | WO 2016/007604 A1 | 1/2016 |
| WO | WO 2016/025759 A1 | 2/2016 |
| WO | WO 2016/033315 A2 | 3/2016 |
| WO | WO 2016/100389 A1 | 6/2016 |
| WO | WO 2016/109255 A1 | 7/2016 |
| WO | WO 2016/130697 A1 | 8/2016 |
| WO | WO 2017/165565 A1 | 9/2017 |
| WO | WO 2018/013990 A1 | 1/2018 |
| WO | WO 2018/048827 A1 | 3/2018 |
| WO | WO 2018/148511 A1 | 8/2018 |
| WO | WO 2019/018534 A1 | 1/2019 |
| WO | WO 2020/206134 A1 | 10/2020 |

OTHER PUBLICATIONS

Wang et al "ExoCET: exonuclease in vitro assembly combined with RecET recombination for highly efficient direct DNA cloning from complex genomes" (Nucleic Acids Research, 2018, vol. 46, No. 5 published Dec. 12, 2017, pp. 1-11). (Year: 2017).*
Huang et al "A rapid seamless method for gene knockout in Pseudomonas aeruginosa" (Microbiology 2017 vol. 17, pp. 1-8). (Year: 2017).*
"Frequencies of Restriction Sites," New England BioLabs Inc. [Retrieved from the Internet Oct. 23, 2016: https://www.neb.com/tools-and-resources/selection-charts/frequencies-of-restriction-sites?device=PDF].
Anderson et al., "BglBricks: A flexible standard for biological part assembly," Journal of Biological Engineering, 4(1):1, pp. 1-12, (2010).
Casini et al., "Bricks and blueprints: methods and standards for DNA assembly," Nature Reviews, 16(9):568-576, (2015).
Casini, "Advanced DNA assembly strategies and standards for synthetic biology," (PhD Thesis), (2014). [Retrieved from the Internet Dec. 16, 2015: https://spiral.imperial.ac.uk/bitstream/10044/1/25291/1/Casini-A-2015-PhD-Thesis.pdf>].
Chao et al., "Recent advances in DNA assembly technologies," FEMS Yeast Research,15(1):1-9, (2015).
De Kok et al., "Rapid and Reliable DNA Assembly via Ligase Cycling Reaction," ACS Synthetic Biology, 3(2):97-106, (2014).
Gibson et al., "Enzymatic assembly of DNA molecules up to several hundred kilobases," Nature Methods, 6(5):343-345 and Supplementary Materials, (2009).

(Continued)

*Primary Examiner* — Catherine S Hibbert
(74) *Attorney, Agent, or Firm* — Yongjin Choi; Alston & Bird LLP

(57) ABSTRACT

Methods for introducing a scarless targeted genetic modification into a preexisting targeting vector are provided. The methods can use combinations of bacterial homologous recombination (BHR) and in vitro assembly to introduce such targeted genetic modifications into a preexisting targeting vector in a scarless manner.

29 Claims, 5 Drawing Sheets

Specification includes a Sequence Listing.

(56) References Cited

OTHER PUBLICATIONS

Gibson, "Chapter Fifteen: Enzymatic Assembly of Overlapping DNA Fragments," Methods in Enzymology, 498:349-361, (2011).
Halleran et al., "Single Day Construction of Multigene Circuits with 3G Assembly," ACS Synth. Biol., 7(5):1477-1480, (2018).
Holowachuk et al., "Efficient Gene Synthesis by Klenow Assembly/Extension-Pfu Polymerase Amplification (KAPPA) of Overlapping Oligonucleotides," Genome Research, 4(5):299-302, (1995).
Karvelis et al., "Programmable DNA cleavage in vitroby Cas9," BioChem. Soc. Trans., 41(6):1401-1406, (2013).
Lee et al., "Emerging Tools for Synthetic Genome Design," Mol. Cells, 35(5):359-370, (2013).
Lee et al., "Highly efficient CRISPR/Cas9-mediated TAR cloning of genes and chromosomal loci from complex genomes in yeast," Nucleic Acids Research, 43(8):e55, pp. 1-9, (2015).
Li et al., "Harnessing homologous recombination in vitro to generate recombinant DNA via SLIC," Nature Methods, 4(3):251-256, (2007).
Maresca et al., "Obligate Ligation-Gated Recombination (ObLiGaRe): Custom-designed nuclease-mediated targeted integration through nonhomologous end joining," Genome Res., 23(3):539-546, (2012).
Merryman et al., "Methods and applications for assembling large DNA constructs," Metabolic Engineering, 14(3):196-204, (2012).
Orlando et al., "Zinc-finger nuclease-driven targeted integration into mammalian genomes using donors with limited chromosomal homology," Nucleic Acids Res., 38(15):e152, pp. 1-15, (2010).
Ramon et al., "Single-step linker-based combinatorial assembly of promoter and gene cassettes for pathway engineering," Biotechnol. Lett., 33(3):549-555, (2010).
Ran et al., "Double Nicking by RNA-Guided CRISPR Cas9 for Enhanced Genome Editing Specificity," Cell, 154(6):1380-1389, (2013).
Roth et al., "A Rapid and Simple Method for DNA Engineering Using Cycled Ligation Assembly," PLoS One, 9(9):e107329, pp. 1-9, (2014).
Stevenson et al., "A Practical Comparison of Ligation-Independent Cloning Techniques," PLoS One, 8(12):e83888, pp. 1-7, (2013).
Trubitsyna et al., "PaperClip: rapid mutli-part DNA assembly from existing libraries," Nucleic Acids Research, 42(20):e154, pp. 1-8, (2014).
Tsvetanova et al., "Chapter Fourteen: Genetic Assembly Tools for Synthetic Biology," Methods in Enzymology, 498:327-348, (2011).
Valenzuela et al., "High-throughput engineering of the mouse genome coupled with high-resolution expression analysis," Nat. Biotechnol., 21(6):652-659, (2003).
Vroom et al., "Modular construction of plasmids through ligation-free assembly of vector components with oligonucleotide linkers," Biotechniques, 44(7):924-926, (2008).
Wang et al., "CRISPR/Cas9 nuclease cleavage combined with Gibson assembly for seamless cloning," Biotechniques, 58(4):161-170 (2015).
Wang et al., "DNA Fragments Assembly Based on Nicking Enzyme System," PLoS ONE, 8(3):e57943, pp. 1-12, (2013).
Zhao et al., "Realizing directional cloning using sticky ends produced by 3'-5' exonuclease of Klenow fragment," J. Biosci., 38(5):857-866, (2013).
Chandran et al., "TREC-IN: gene knock-in genetic tool for genomes cloned in yeast," BMC Genomics, 15(1):1180, 11 pages, (2014).
Sung et al., "Scarless chromosomal gene knockout methods," Methods Mol. Biol., 765:43-54, (2011).
Liang and Liu, "Scarless and sequential gene modification in Pseuomonas using PCR product flanked by short homology regions," BMC Microbiol., 10:209, 9 pages, (2010).
Yang et al., "High-Efficiency Scarless Genetic Modification in *Escherichia coli* by Using Lambda Red Recombination and I-SceI Cleavage," Appl. Environ. Microbiol., 80(13):3826-3834,(2014).
Yu et al., "Rapid and efficient construction of markerless deletions in the *Escherichia coli* genome," Nucleic Acids Res., 36(14):e84, 8 pages, (2008).
WIPO Application No. PCT/US2020/026405, PCT International Search Report and Written Opinion of the International Searching Authority dated Jul. 8, 2020.

* cited by examiner

US 11,111,504 B2

```
                         SEQUENCE LISTING

<160> NUMBER OF SEQ ID NOS: 16

<210> SEQ ID NO 1
<211> LENGTH: 1370
<212> TYPE: PRT
<213> ORGANISM: Artificial Sequence
<220> FEATURE:
<223> OTHER INFORMATION: Synthetic

<400> SEQUENCE: 1

Gly Ala Ala Ser Asp Lys Lys Tyr Ser Ile Gly Leu Asp Ile Gly Thr
1               5                  10                  15

Asn Ser Val Gly Trp Ala Val Ile Thr Asp Glu Tyr Lys Val Pro Ser
            20                  25                  30

Lys Lys Phe Lys Val Leu Gly Asn Thr Asp Arg His Ser Ile Lys Lys
        35                  40                  45

Asn Leu Ile Gly Ala Leu Leu Phe Asp Ser Gly Glu Thr Ala Glu Ala
    50                  55                  60

Thr Arg Leu Lys Arg Thr Ala Arg Arg Arg Tyr Thr Arg Arg Lys Asn
65                  70                  75                  80

Arg Ile Cys Tyr Leu Gln Glu Ile Phe Ser Asn Glu Met Ala Lys Val
                85                  90                  95

Asp Asp Ser Phe Phe His Arg Leu Glu Glu Ser Phe Leu Val Glu Glu
            100                 105                 110

Asp Lys Lys His Glu Arg His Pro Ile Phe Gly Asn Ile Val Asp Glu
        115                 120                 125

Val Ala Tyr His Glu Lys Tyr Pro Thr Ile Tyr His Leu Arg Lys Lys
    130                 135                 140

Leu Val Asp Ser Thr Asp Lys Ala Asp Leu Arg Leu Ile Tyr Leu Ala
145                 150                 155                 160

Leu Ala His Met Ile Lys Phe Arg Gly His Phe Leu Ile Glu Gly Asp
                165                 170                 175

Leu Asn Pro Asp Asn Ser Asp Val Asp Lys Leu Phe Ile Gln Leu Val
            180                 185                 190

Gln Thr Tyr Asn Gln Leu Phe Glu Glu Asn Pro Ile Asn Ala Ser Gly
        195                 200                 205

Val Asp Ala Lys Ala Ile Leu Ser Ala Arg Leu Ser Lys Ser Arg Arg
    210                 215                 220

Leu Glu Asn Leu Ile Ala Gln Leu Pro Gly Glu Lys Lys Asn Gly Leu
225                 230                 235                 240

Phe Gly Asn Leu Ile Ala Leu Ser Leu Gly Leu Thr Pro Asn Phe Lys
```

```
                245                 250                 255
Ser Asn Phe Asp Leu Ala Glu Asp Ala Lys Leu Gln Leu Ser Lys Asp
            260                 265                 270

Thr Tyr Asp Asp Leu Asp Asn Leu Leu Ala Gln Ile Gly Asp Gln
        275                 280                 285

Tyr Ala Asp Leu Phe Leu Ala Ala Lys Asn Leu Ser Asp Ala Ile Leu
        290                 295                 300

Leu Ser Asp Ile Leu Arg Val Asn Thr Glu Ile Thr Lys Ala Pro Leu
305                 310                 315                 320

Ser Ala Ser Met Ile Lys Arg Tyr Asp Glu His His Gln Asp Leu Thr
                325                 330                 335

Leu Leu Lys Ala Leu Val Arg Gln Gln Leu Pro Glu Lys Tyr Lys Glu
                340                 345                 350

Ile Phe Phe Asp Gln Ser Lys Asn Gly Tyr Ala Gly Tyr Ile Asp Gly
            355                 360                 365

Gly Ala Ser Gln Glu Glu Phe Tyr Lys Phe Ile Lys Pro Ile Leu Glu
        370                 375                 380

Lys Met Asp Gly Thr Glu Glu Leu Leu Val Lys Leu Asn Arg Glu Asp
385                 390                 395                 400

Leu Leu Arg Lys Gln Arg Thr Phe Asp Asn Gly Ser Ile Pro His Gln
                405                 410                 415

Ile His Leu Gly Glu Leu His Ala Ile Leu Arg Arg Gln Glu Asp Phe
            420                 425                 430

Tyr Pro Phe Leu Lys Asp Asn Arg Glu Lys Ile Glu Lys Ile Leu Thr
        435                 440                 445

Phe Arg Ile Pro Tyr Tyr Val Gly Pro Leu Ala Arg Gly Asn Ser Arg
450                 455                 460

Phe Ala Trp Met Thr Arg Lys Ser Glu Glu Thr Ile Thr Pro Trp Asn
465                 470                 475                 480

Phe Glu Glu Val Val Asp Lys Gly Ala Ser Ala Gln Ser Phe Ile Glu
                485                 490                 495

Arg Met Thr Asn Phe Asp Lys Asn Leu Pro Asn Glu Lys Val Leu Pro
            500                 505                 510

Lys His Ser Leu Leu Tyr Glu Tyr Phe Thr Val Tyr Asn Glu Leu Thr
        515                 520                 525

Lys Val Lys Tyr Val Thr Glu Gly Met Lys Pro Ala Phe Leu Ser Gly
        530                 535                 540

Glu Gln Lys Lys Ala Ile Val Asp Leu Leu Phe Lys Thr Asn Arg Lys
545                 550                 555                 560

Val Thr Val Lys Gln Leu Lys Glu Asp Tyr Phe Lys Lys Ile Glu Cys
                565                 570                 575

Phe Asp Ser Val Glu Ile Ser Gly Val Glu Asp Arg Phe Asn Ala Ser
            580                 585                 590

Leu Gly Thr Tyr His Asp Leu Leu Lys Ile Ile Lys Asp Lys Asp Phe
        595                 600                 605

Leu Asp Asn Glu Glu Asn Glu Asp Ile Leu Glu Asp Ile Val Leu Thr
        610                 615                 620

Leu Thr Leu Phe Glu Asp Arg Glu Met Ile Glu Glu Arg Leu Lys Thr
625                 630                 635                 640

Tyr Ala His Leu Phe Asp Asp Lys Val Met Lys Gln Leu Lys Arg Arg
                645                 650                 655

Arg Tyr Thr Gly Trp Gly Arg Leu Ser Arg Lys Leu Ile Asn Gly Ile
            660                 665                 670
```

```
Arg Asp Lys Gln Ser Gly Lys Thr Ile Leu Asp Phe Leu Lys Ser Asp
            675                 680                 685

Gly Phe Ala Asn Arg Asn Phe Met Gln Leu Ile His Asp Asp Ser Leu
690                 695                 700

Thr Phe Lys Glu Asp Ile Gln Lys Ala Gln Val Ser Gly Gln Gly Asp
705                 710                 715                 720

Ser Leu His Glu His Ile Ala Asn Leu Ala Gly Ser Pro Ala Ile Lys
                725                 730                 735

Lys Gly Ile Leu Gln Thr Val Lys Val Val Asp Glu Leu Val Lys Val
                740                 745                 750

Met Gly Arg His Lys Pro Glu Asn Ile Val Ile Glu Met Ala Arg Glu
            755                 760                 765

Asn Gln Thr Thr Gln Lys Gly Gln Lys Asn Ser Arg Glu Arg Met Lys
770                 775                 780

Arg Ile Glu Glu Gly Ile Lys Glu Leu Gly Ser Gln Ile Leu Lys Glu
785                 790                 795                 800

His Pro Val Glu Asn Thr Gln Leu Gln Asn Glu Lys Leu Tyr Leu Tyr
                805                 810                 815

Tyr Leu Gln Asn Gly Arg Asp Met Tyr Val Asp Gln Glu Leu Asp Ile
                820                 825                 830

Asn Arg Leu Ser Asp Tyr Asp Val Asp His Ile Val Pro Gln Ser Phe
835                 840                 845

Leu Lys Asp Asp Ser Ile Asp Asn Lys Val Leu Thr Arg Ser Asp Lys
850                 855                 860

Asn Arg Gly Lys Ser Asp Asn Val Pro Ser Glu Glu Val Val Lys Lys
865                 870                 875                 880

Met Lys Asn Tyr Trp Arg Gln Leu Leu Asn Ala Lys Leu Ile Thr Gln
                885                 890                 895

Arg Lys Phe Asp Asn Leu Thr Lys Ala Glu Arg Gly Gly Leu Ser Glu
                900                 905                 910

Leu Asp Lys Ala Gly Phe Ile Lys Arg Gln Leu Val Glu Thr Arg Gln
            915                 920                 925

Ile Thr Lys His Val Ala Gln Ile Leu Asp Ser Arg Met Asn Thr Lys
            930                 935                 940

Tyr Asp Glu Asn Asp Lys Leu Ile Arg Glu Val Lys Val Ile Thr Leu
945                 950                 955                 960

Lys Ser Lys Leu Val Ser Asp Phe Arg Lys Asp Phe Gln Phe Tyr Lys
                965                 970                 975

Val Arg Glu Ile Asn Asn Tyr His His Ala His Asp Ala Tyr Leu Asn
                980                 985                 990

Ala Val Val Gly Thr Ala Leu Ile Lys Lys Tyr Pro Lys Leu Glu Ser
            995                 1000                1005

Glu Phe Val Tyr Gly Asp Tyr Lys Val Tyr Asp Val Arg Lys Met
    1010                1015                1020

Ile Ala Lys Ser Glu Gln Glu Ile Gly Lys Ala Thr Ala Lys Tyr
    1025                1030                1035

Phe Phe Tyr Ser Asn Ile Met Asn Phe Phe Lys Thr Glu Ile Thr
    1040                1045                1050

Leu Ala Asn Gly Glu Ile Arg Lys Arg Pro Leu Ile Glu Thr Asn
    1055                1060                1065

Gly Glu Thr Gly Glu Ile Val Trp Asp Lys Gly Arg Asp Phe Ala
    1070                1075                1080
```

```
Thr Val Arg Lys Val Leu Ser Met Pro Gln Val Asn Ile Val Lys
1085                1090                1095

Lys Thr Glu Val Gln Thr Gly Gly Phe Ser Lys Glu Ser Ile Leu
1100                1105                1110

Pro Lys Arg Asn Ser Asp Lys Leu Ile Ala Arg Lys Lys Asp Trp
1115                1120                1125

Asp Pro Lys Lys Tyr Gly Gly Phe Asp Ser Pro Thr Val Ala Tyr
1130                1135                1140

Ser Val Leu Val Val Ala Lys Val Glu Lys Gly Lys Ser Lys Lys
1145                1150                1155

Leu Lys Ser Val Lys Glu Leu Leu Gly Ile Thr Ile Met Glu Arg
1160                1165                1170

Ser Ser Phe Glu Lys Asn Pro Ile Asp Phe Leu Glu Ala Lys Gly
1175                1180                1185

Tyr Lys Glu Val Lys Lys Asp Leu Ile Ile Lys Leu Pro Lys Tyr
1190                1195                1200

Ser Leu Phe Glu Leu Glu Asn Gly Arg Lys Arg Met Leu Ala Ser
1205                1210                1215

Ala Gly Glu Leu Gln Lys Gly Asn Glu Leu Ala Leu Pro Ser Lys
1220                1225                1230

Tyr Val Asn Phe Leu Tyr Leu Ala Ser His Tyr Glu Lys Leu Lys
1235                1240                1245

Gly Ser Pro Glu Asp Asn Glu Gln Lys Gln Leu Phe Val Glu Gln
1250                1255                1260

His Lys His Tyr Leu Asp Glu Ile Ile Glu Gln Ile Ser Glu Phe
1265                1270                1275

Ser Lys Arg Val Ile Leu Ala Asp Ala Asn Leu Asp Lys Val Leu
1280                1285                1290

Ser Ala Tyr Asn Lys His Arg Asp Lys Pro Ile Arg Glu Gln Ala
1295                1300                1305

Glu Asn Ile Ile His Leu Phe Thr Leu Thr Asn Leu Gly Ala Pro
1310                1315                1320

Ala Ala Phe Lys Tyr Phe Asp Thr Thr Ile Asp Arg Lys Arg Tyr
1325                1330                1335

Thr Ser Thr Lys Glu Val Leu Asp Ala Thr Leu Ile His Gln Ser
1340                1345                1350

Ile Thr Gly Leu Tyr Glu Thr Arg Ile Asp Leu Ser Gln Leu Gly
1355                1360                1365

Gly Asp
1370

<210> SEQ ID NO 2
<211> LENGTH: 4104
<212> TYPE: DNA
<213> ORGANISM: Artificial Sequence
<220> FEATURE:
<223> OTHER INFORMATION: Synthetic

<400> SEQUENCE: 2
gataagaaat actcaatagg cttagatatc ggcacaaata gcgtcggatg ggcggtgatc      60
actgatgaat ataaggttcc gtctaaaaag ttcaaggttc tgggaaatac agaccgccac     120
agtatcaaaa aaaatcttat aggggctctt ttatttgaca gtggagagac agcggaagcg     180
actcgtctca acggacagc tcgtagaagg tatacgtc ggaagaatcg tatttgttat       240
ctacaggaga ttttttcaaa tgagatggcg aaagtagatg atagtttctt tcatcgactt     300
```

```
gaagagtctt ttttggtgga agaagacaag aagcatgaac gtcatcctat ttttggaaat    360
atagtagatg aagttgctta tcatgagaaa tatccaacta tctatcatct gcgaaaaaaa    420
ttggtagatt ctactgataa agcggatttg cgcttaatct atttggcctt agcgcatatg    480
attaagtttc gtggtcattt tttgattgag ggagatttaa atcctgataa tagtgatgtg    540
gacaaactat ttatccagtt ggtacaaacc tacaatcaat tatttgaaga aaaccctatt    600
aacgcaagtg gagtagatgc taaagcgatt ctttctgcac gattgagtaa atcaagacga    660
ttagaaaatc tcattgctca gctccccggt gagaagaaaa atggcttatt tgggaatctc    720
attgctttgt cattgggttt gacccctaat tttaaatcaa attttgattt ggcagaagat    780
gctaaattac agctttcaaa agatacttac gatgatgatt tagataattt attggcgcaa    840
attggagatc aatatgctga tttgttttg gcagctaaga atttatcaga tgctatttta    900
ctttcagata tcctaagagt aaatactgaa ataactaagg ctcccctatc agcttcaatg    960
attaaacgct acgatgaaca tcatcaagac ttgactcttt taaaagcttt agttcgacaa   1020
caacttccag aaaagtataa agaaatcttt tttgatcaat caaaaaacgg atatgcaggt   1080
tatattgatg ggggagctag ccaagaagaa ttttataaat ttatcaaacc aattttagaa   1140
aaaatggatg gtactgagga attattggtg aaactaaatc gtgaagattt gctgcgcaag   1200
caacggacct tgacaacgg ctctattccc catcaaattc acttgggtga gctgcatgct   1260
attttgagaa gacaagaaga cttttatcca ttttaaaag acaatcgtga aagattgaa   1320 aaaatcttga cttttcgaat tccttattat gttggtccat ggcgcgtgg caatagtcgt   1380 tttgcatgga tgactcggaa gtctgaagaa acaattaccc catggaattt tgaagaagtt   1440
gtcgataaag gtgcttcagc tcaatcattt attgaacgca tgacaaactt tgataaaaat   1500
cttccaaatg aaaagtact accaaaacat agtttgcttt atgagtattt tacggtttat   1560
aacgaattga caaggtcaa atatgttact gaaggaatgc gaaaaccagc atttctttca   1620
ggtgaacaga agaaagccat tgttgattta ctcttcaaaa caaatcgaaa agtaaccgtt   1680
aagcaattaa aagaagatta tttcaaaaaa atagaatgtt ttgatagtgt tgaaatttca   1740
ggagttgaag atagatttaa tgcttcatta ggtacctacc atgatttgct aaaaattatt   1800
aaagataaag atttttgga taatgaagaa aatgaagata tcttagagga tattgtttta   1860
acattgacct tatttgaaga tagggagatg attgaggaaa gacttaaaac atatgctcac   1920
ctctttgatg ataaggtgat gaaacagctt aaacgtcgcc gttatactgg ttggggacgt   1980
ttgtctcgaa aattgattaa tggtattagg ataagcaat ctggcaaaac aatattagat   2040
tttttgaaat cagatggttt tgccaatcgc aattttatgc agctgatcca tgatgatagt   2100
ttgacattta aagaagacat tcaaaaagca caagtgtctg acaaggcga tagtttacat   2160 gaacatattg caaatttagc tggtagccct gctattaaaa aaggtatttt acagactgta   2220
aaagttgttg atgaattggt caagtaatg gggcggcata agccagaaaa tatcgttatt   2280
gaaatggcac gtgaaaatca gacaactcaa aagggccaga aaaattcgcg agagcgtatg   2340
aaacgaatcg aagaaggtat caagaatta ggaagtcaga ttcttaaaga gcatcctgtt   2400
gaaaatactc aattgcaaaa tgaaaagctc tatctctatt atctccaaaa tggaagagac   2460
atgtatgtgg accaagaatt agatattaat cgtttaagtg attatgatgt cgatcacatt   2520
gttccacaaa gtttccttaa agacgattca atagacaata aggtcttaac gcgttctgat   2580
aaaaatcgtg gtaaatcgga taacgttcca agtgaagaag tagtcaaaaa gatgaaaaac   2640
```

```
tattggagac aacttctaaa cgccaagtta atcactcaac gtaagtttga taatttaacg    2700
aaagctgaac gtggaggttt gagtgaactt gataaagctg gttttatcaa acgccaattg    2760
gttgaaactc gccaaatcac taagcatgtg gcacaaattt tggatagtcg catgaatact    2820
aaatacgatg aaaatgataa acttattcga gaggttaaag tgattacctt aaaatctaaa    2880
ttagtttctg acttccgaaa agatttccaa ttctataaag tacgtgagat taacaattac    2940
catcatgccc atgatgcgta tctaaatgcc gtcgttggaa ctgctttgat taagaaatat    3000
ccaaaacttg aatcggagtt tgtctatggt gattataaag tttatgatgt tcgtaaaatg    3060
attgctaagt ctgagcaaga aataggcaaa gcaaccgcaa atatttctt ttactctaat    3120 atcatgaact tcttcaaaac agaaattaca cttgcaaatg gagagattcg caaacgccct    3180
ctaatcgaaa ctaatgggga aactggagaa attgtctggg ataaagggcg agattttgcc    3240
acagtgcgca aagtattgtc catgccccaa gtcaatattg tcaagaaaac agaagtacag    3300
acaggcggat tctccaagga gtcaattta ccaaaagaa attcggacaa gcttattgct    3360 cgtaaaaag actgggatcc aaaaaatat ggtggttttg atagtccaac ggtagcttat    3420
tcagtcctag tggttgctaa ggtggaaaaa gggaaatcga agaagttaaa atccgttaaa    3480
gagttactag ggatcacaat tatggaaaga agttcctttg aaaaaaatcc gattgacttt    3540
ttagaagcta aaggatataa ggaagttaaa aaagacttaa tcattaaact acctaaaatat    3600 agtcttttg agttagaaaa cggtcgtaaa cggatgctgg ctagtgccgg agaattacaa    3660
aaaggaaatg agctggctct gccaagcaaa tatgtgaatt ttttatattt agctagtcat    3720
tatgaaaagt tgaagggtag tccagaagat aacgaacaaa aacaattgtt tgtgggagcag    3780 cataagcatt atttagatga gattattgag caaatcagtg aatttctaa gcgtgttatt    3840 ttagcagatg ccaattaga taaagttctt agtgcatata caaacatag agacaaacca    3900 atacgtgaac aagcagaaaa tattattcat ttatttacgt tgacgaatct tggagctccc    3960
gctgctttta atatttga tacaacaatt gatcgtaaac gatatacgtc tacaaaagaa    4020
gttttagatg ccactcttat ccatcaatcc atcactggtc tttatgaaac acgcattgat    4080
ttgagtcagc taggaggtga ctga                                           4104

<210> SEQ ID NO 3
<211> LENGTH: 16
<212> TYPE: RNA
<213> ORGANISM: Artificial Sequence
<220> FEATURE:
<223> OTHER INFORMATION: Synthetic

<400> SEQUENCE: 3
guuuuagagc uaugcu                                                    16

<210> SEQ ID NO 4
<211> LENGTH: 67
<212> TYPE: RNA
<213> ORGANISM: Artificial Sequence
<220> FEATURE:
<223> OTHER INFORMATION: Synthetic

<400> SEQUENCE: 4
agcauagcaa guuaaaauaa ggcuaguccg uuaucaacuu gaaaaagugg caccgagucg    60
gugcuuu                                                              67

<210> SEQ ID NO 5
<211> LENGTH: 77
```

```
<212> TYPE: RNA
<213> ORGANISM: Artificial Sequence
<220> FEATURE:
<223> OTHER INFORMATION: Synthetic

<400> SEQUENCE: 5
guuuuagagc uagaaauagc aaguuaaaau aaggcuaguc cguuaucaac uugaaaaagu    60
ggcaccgagu cggugcu                                                  77

<210> SEQ ID NO 6
<211> LENGTH: 82
<212> TYPE: RNA
<213> ORGANISM: Artificial Sequence
<220> FEATURE:
<223> OTHER INFORMATION: Synthetic

<400> SEQUENCE: 6
guuggaacca uucaaaacag cauagcaagu uaaaauaagg cuaguccguu aucaacuuga    60
aaaaguggca ccgagucggu gc                                            82

<210> SEQ ID NO 7
<211> LENGTH: 76
<212> TYPE: RNA
<213> ORGANISM: Artificial Sequence
<220> FEATURE:
<223> OTHER INFORMATION: Synthetic

<400> SEQUENCE: 7
guuuuagagc uagaaauagc aaguuaaaau aaggcuaguc cguuaucaac uugaaaaagu    60
ggcaccgagu cggugc                                                   76

<210> SEQ ID NO 8
<211> LENGTH: 86
<212> TYPE: RNA
<213> ORGANISM: Artificial Sequence
<220> FEATURE:
<223> OTHER INFORMATION: Synthetic

<400> SEQUENCE: 8
guuuaagagc uaugcuggaa acagcauagc aaguuuaaau aaggcuaguc cguuaucaac    60
uugaaaaagu ggcaccgagu cggugc                                        86

<210> SEQ ID NO 9
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: n is a, c, g, or t

<400> SEQUENCE: 9
gnnnnnnnnn nnnnnnnnnn ngg                                           23

<210> SEQ ID NO 10
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(21)
```

<223> OTHER INFORMATION: n is a, c, g, or t

<400> SEQUENCE: 10
nnnnnnnnnn nnnnnnnnnn ngg                                    23

<210> SEQ ID NO 11
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(23)
<223> OTHER INFORMATION: n is a, c, g, or t

<400> SEQUENCE: 11
ggnnnnnnnn nnnnnnnnnn nnngg                                  25

<210> SEQ ID NO 12
<211> LENGTH: 72
<212> TYPE: RNA
<213> ORGANISM: Artificial Sequence
<220> FEATURE:
<223> OTHER INFORMATION: Synthetic

<400> SEQUENCE: 12
aaacagcaua gcaaguuaaa auaaggcuag uccguuauca acugaaaaa guggcaccga    60 gucggugcuu uu                                                      72

<210> SEQ ID NO 13
<211> LENGTH: 82
<212> TYPE: RNA
<213> ORGANISM: Artificial Sequence
<220> FEATURE:
<223> OTHER INFORMATION: Synthetic

<400> SEQUENCE: 13
guuggaacca uucaaaacag cauagcaagu uaaauaagg cuaguccguu aucaacuuga    60
aaaaguggca ccgagucggu gc                                           82

<210> SEQ ID NO 14
<211> LENGTH: 83
<212> TYPE: RNA
<213> ORGANISM: Artificial Sequence
<220> FEATURE:
<223> OTHER INFORMATION: Synthetic

<400> SEQUENCE: 14
guuuuagagc uagaaauagc aaguuaaaau aaggcuaguc cguuaucaac uugaaaaagu   60
ggcaccgagu cggugcuuuu uuu                                          83

<210> SEQ ID NO 15
<211> LENGTH: 80
<212> TYPE: RNA
<213> ORGANISM: Artificial Sequence
<220> FEATURE:
<223> OTHER INFORMATION: Synthetic

<400> SEQUENCE: 15
guuuuagagc uagaaauagc aaguuaaaau aaggcuaguc cguuaucaac uugaaaaagu   60
ggcaccgagu cggugcuuuu                                              80

```
<210> SEQ ID NO 16
<211> LENGTH: 92
<212> TYPE: RNA
<213> ORGANISM: Artificial Sequence
<220> FEATURE:
<223> OTHER INFORMATION: Synthetic

<400> SEQUENCE: 16
guuuaagagc uaugcuggaa acagcauagc aaguuuaaau aaggcuaguc cguuaucaac      60
uugaaaaagu ggcaccgagu cggugcuuuu uu                                   92
```

METHODS FOR SCARLESS INTRODUCTION OF TARGETED MODIFICATIONS INTO TARGETING VECTORS

CROSS-REFERENCE TO RELATED APPLICATIONS

This application claims the benefit of U.S. Application No. 62/829,327, filed Apr. 4, 2019, which is herein incorporated by reference in its entirety for all purposes.

REFERENCE TO A SEQUENCE LISTING SUBMITTED AS A TEXT FILE VIA EFS WEB

The Sequence Listing written in file 545017SEQLIST.txt is 20.7 kilobytes, was created on Apr. 2, 2020, and is hereby incorporated by reference.

BACKGROUND

Seamless DNA construction is of particular importance when creating transgenic animal lines, as the scars produced by restriction sites or other manipulations can negatively impact gene expression if they land in a region important for regulation. Targeting the mammalian genome often requires construction of large targeting vectors with long DNA arms to direct homologous recombination, as well as antibiotic resistance cassettes for selection of embryonic stem cell clones. Correctly targeted clones often contain multiple scars necessary for construction of the vector, not to mention the resistance cassette itself. For genetic ablation, these lesions may not matter for the end result (a null allele), but there is always a chance that expression by neighboring genes will be adversely affected. For modifications other than knock-out, such as knock-in, faithful expression of the targeted locus is usually important for the studies in question.

In particular, humanization, the direct replacement of a mouse gene with its human counterpart, requires seamless junctions between mouse and human sequence so that mouse transcription machinery will faithfully replicate expression of the new allele. Care must be taken to bury construction scars and selection cassette in non-coding regions that do not impact gene regulation. As animal models become more complex, more modifications may be added on top of existing ones, such as human disease-causing mutations on top of humanized alleles. The additional changes can then add even more scars and another selection cassette to an already highly engineered mouse locus, increasing the likelihood that expression will be altered and the mouse model will not be faithful to human disease. From a construction standpoint, adding a new cassette to a vector already containing one can become complicated due to undesired recombination between shared cassette elements such as promoters and poly(A) signals, even if the two cassettes encode different selections. Consequently, new methods are needed to simplify the generation of targeting carrying multiple changes (such as a humanized allele and a disease mutation layered on top) and to minimize the scars incorporated into a final animal model.

SUMMARY

Methods of scarless introduction of a targeted genetic modification into a preexisting targeting vector are provided.

In one aspect, some such methods comprise: (a) performing bacterial homologous recombination between the preexisting targeting vector and a modification cassette in a population of bacterial cells, wherein the modification cassette comprises the targeted genetic modification and comprises an insert nucleic acid flanked by a 5' homology arm corresponding to a 5' target sequence in the preexisting targeting vector and a 3' homology arm corresponding to a 3' target sequence in the preexisting vector, wherein the insert nucleic acid comprises from 5' to 3': (i) a first repeat sequence; (ii) a first target site for a first nuclease agent; (iii) a selection cassette; (iv) a second target site for a second nuclease agent; and (v) a second repeat sequence identical to the first repeat sequence; (b) selecting bacterial cells comprising a modified targeting vector comprising the selection cassette; (c) cleaving the first target site in the modified targeting vector with the first nuclease agent and cleaving the second target site in the modified targeting vector with the second nuclease agent to remove the selection cassette and expose the first repeat sequence and the second repeat sequence in the modified targeting vector; and (d) assembling the exposed first repeat sequence with the exposed second repeat sequence in an intramolecular in vitro assembly reaction to generate the targeting vector comprising the scarless targeted genetic modification, wherein neither the first target site for the first nuclease agent nor the second target site for the second nuclease agent are present and only a single copy of the repeat sequence is present in the targeting vector comprising the scarless targeted genetic modification.

In some such methods, the repeat sequence is identical to a sequence in the preexisting targeting vector. In some such methods, the targeted genetic modification comprises an insertion, and the repeat sequence is identical to the 5' end or the 3' end of the insertion.

In some such methods, the repeat sequence is at least about 20 nucleotides in length. Optionally, the repeat sequence is between about 20 nucleotides and about 100 nucleotides in length.

In some such methods, the modification cassette is a linear, double-stranded nucleic acid. In some such methods, the modification cassette is from about 1 kb to about 15 kb in length. In some such methods, the 5' homology arm and the 3' homology arm are each at least about 35 nucleotides in length. In some such methods, the 5' homology arm and the 3' homology arm are each between about 35 nucleotides and about 500 nucleotides in length.

In some such methods, the first nuclease agent and/or the second nuclease agent is a rare-cutting nuclease agent. In some such methods, the first target site and/or the second target site is not present in the preexisting targeting vector. In some such methods, the first target site is identical to the second target site, and the first nuclease agent is identical to the second nuclease agent.

In some such methods, the first nuclease agent and/or the second nuclease agent comprises a rare-cutting restriction enzyme. Optionally, the rare-cutting restriction enzyme is NotI, XmaIII, SstII, SalI, NruI, NheI, Nb.BbvCI, BbvCI, AscI, AsiSI, FseI, PacI, PmeI, SbfI, SgrAI, SwaI, BspQI, SapI, SfiI, CspCI, AbsI, CciNI, FspAI, MauBI, MreI, MssI, PalAI, RgaI, RigI, SdaI, SfaAI, SgfI, SgrDI, SgsI, SmiI, SrfI, Sse2321, Sse83871, LguI, PciSI, AarI, AjuI, AloI, BarI, PpiI, or PsrI.

In some such methods, the first nuclease agent and/or the second nuclease agent is a Clustered Regularly Interspaced Short Palindromic Repeats (CRISPR)-associated (Cas) protein and a guide RNA (gRNA), a zinc finger nuclease (ZFN), a Transcription Activator-Like Effector Nuclease (TALEN), or an engineered meganuclease. Optionally, the first nuclease agent and/or the second nuclease agent the Cas protein and the gRNA, wherein the Cas protein is Cas9, and wherein the gRNA comprises a CRISPR RNA (crRNA) that targets and a trans-activating CRIPSR RNA (tracrRNA).

In some such methods, the targeted genetic modification comprises a modification in the 5' homology arm or the 3' homology arm. In some such methods, the targeted genetic modification comprises a modification in the insert nucleic acid. In some such methods, the targeted genetic modification comprises a point mutation, a deletion, an insertion, a replacement, or a combination thereof.

In some such methods, the selection cassette imparts resistance to an antibiotic. Optionally, the selection cassette imparts resistance to ampicillin, chloramphenicol, tetracycline, kanamycin, spectinomycin, streptomycin, carbenicillin, bleomycin, erythromycin, or polymyxin B.

In some such methods, the preexisting targeting vector is a large targeting vector at least about 10 kb in length. Optionally, the preexisting targeting vector is at least about 100 kb in length.

In some such methods, the preexisting targeting vector comprises a second selection cassette. Optionally, the second selection cassette imparts resistance to an antibiotic. Optionally, the selection cassette in the modification cassette and the second selection cassette in the preexisting targeting vector each imparts resistance to a different antibiotic. Optionally, the second selection cassette allows for selection in both bacterial and mammalian cells.

In some such methods, step (c) occurs in vitro.

In some such methods, step (d) comprises: (i) contacting the modified targeting vector with an exonuclease to expose complementary sequences between the first repeat sequence and the second repeat sequence; (ii) annealing the exposed complementary sequences; (iii) extending the 3' ends of the annealed complementary sequences; and (iv) ligating the annealed complementary sequence. Optionally, step (d) comprises incubating the modified targeting vector with an exonuclease, a DNA polymerase, and a DNA ligase.

Some such methods further comprise: (e) treating the targeting vector with the first nuclease agent and the second nuclease agent following the in vitro assembly in step (d) to verify that neither the first target site for the first nuclease agent nor the second target site for the second nuclease agent are present.

In another aspect, some such methods comprise: (a) performing bacterial homologous recombination between the preexisting targeting vector and a deletion cassette in a population of bacterial cells, wherein the deletion cassette comprises an insert nucleic acid flanked by a 5' homology arm corresponding to a 5' target sequence in the preexisting targeting vector and a 3' homology arm corresponding to a 3' target sequence in the preexisting vector, wherein the 5' target sequence and the 3' target sequence flank a region of the preexisting targeting vector into which the targeted genetic modification is to be introduced, and wherein the insert nucleic acid comprises from 5' to 3': (i) a first target site for a first nuclease agent; (ii) a selection cassette; and (iii) a second target site for a second nuclease agent; (b) selecting bacterial cells comprising a modified targeting vector comprising the selection cassette; (c) cleaving the first target site in the modified targeting vector with the first nuclease agent and cleaving the second target site in the modified targeting vector with the second nuclease agent to remove the selection cassette and expose an upstream end sequence and a downstream end sequence in the modified targeting vector; and (d) assembling in an in vitro assembly reaction the cleaved targeting vector with a modification cassette comprising the targeted genetic modification flanked by an upstream end sequence overlapping the upstream end sequence in the modified targeting vector and a downstream end sequence overlapping the downstream end sequence in the modified targeting vector to generate the targeting vector comprising the scarless targeted genetic modification, wherein neither the first target site for the first nuclease agent nor the second target site for the second nuclease agent are present in the targeting vector comprising the scarless targeted genetic modification.

In some such methods, the deletion cassette is from about 1 kb to about 15 kb in length. In some such methods, the 5' homology arm and the 3' homology arm are each at least about 35 nucleotides in length. Optionally, the 5' homology arm and the 3' homology arm are each between about 35 nucleotides and about 500 nucleotides in length. In some such methods, the deletion cassette is a linear, double-stranded nucleic acid.

In some such methods, the first nuclease agent and/or the second nuclease agent is a rare-cutting nuclease agent. In some such methods, the first target site and/or the second target site is not present in the preexisting targeting vector. In some such methods, the first target site is identical to the second target site, and the first nuclease agent is identical to the second nuclease agent.

In some such methods, the first nuclease agent and/or the second nuclease agent comprises a rare-cutting restriction enzyme. Optionally, the rare-cutting restriction enzyme is NotI, XmaIII, SstII, SalI, NruI, NheI, Nb.BbvCI, BbvCI, AscI, AsiSI, FseI, PacI, PmeI, SbfI, SgrAI, SwaI, BspQI, SapI, SfiI, CspCI, AbsI, CciNI, FspAI, MauBI, MreI, MssI, PalAI, RgaI, RigI, SdaI, SfaAI, SgfI, SgrDI, SgsI, SmiI, SrfI, Sse2321, Sse83871, LguI, PciSI, AarI, AjuI, AloI, BarI, PpiI, or PsrI.

In some such methods, the first nuclease agent and/or the second nuclease agent is a Clustered Regularly Interspaced Short Palindromic Repeats (CRISPR)-associated (Cas) protein and a guide RNA (gRNA), a zinc finger nuclease (ZFN), a Transcription Activator-Like Effector Nuclease (TALEN), or an engineered meganuclease. Optionally, the first nuclease agent and/or the second nuclease agent the Cas protein and the gRNA, wherein the Cas protein is Cas9, and wherein the gRNA comprises a CRISPR RNA (crRNA) that targets and a trans-activating CRIPSR RNA (tracrRNA).

In some such methods, the selection cassette imparts resistance to an antibiotic. Optionally, the selection cassette imparts resistance to ampicillin, chloramphenicol, tetracycline, kanamycin, spectinomycin, streptomycin, carbenicillin, bleomycin, erythromycin, or polymyxin B.

In some such methods, the preexisting targeting vector is a large targeting vector at least 10 kb in length. Optionally, the preexisting targeting vector is at least 100 kb in length.

In some such methods, the preexisting targeting vector comprises a second selection cassette. Optionally, the second selection cassette imparts resistance to an antibiotic. Optionally, the selection cassette in the deletion cassette and the second selection cassette in the preexisting targeting vector each imparts resistance to a different antibiotic. Optionally, the second selection cassette allows for selection in both bacterial and mammalian cells.

In some such methods, the length of the overlap between the upstream end sequence in the modification cassette and the upstream end sequence in the modified targeting vector and/or the length of the overlap between the downstream end sequence in the modification cassette and the downstream end sequence in the modified targeting vector is at least about 20 nucleotides in length. In some such methods, the length of the overlap between the upstream end sequence in the modification cassette and the upstream end sequence in the modified targeting vector and/or the length of the overlap between the downstream end sequence in the modification cassette and the downstream end sequence in the modified targeting vector is between about 20 and about 100 nucleotides in length.

In some such methods, wherein step (c) occurs in vitro.

In some such methods, step (d) comprises: (i) contacting the cleaved targeting vector and the modification cassette with an exonuclease to expose complementary sequences between the end sequences in the modified targeting vector and the end sequences in the modification cassette; (ii) annealing the exposed complementary sequences; (iii) extending the 3' ends of the annealed complementary sequences; and (iv) ligating the annealed complementary sequence. Optionally, step (d) comprises incubating the cleaved targeting vector and the modification cassette with an exonuclease, a DNA polymerase, and a DNA ligase.

In some such methods, the modification cassette is a linear, double-stranded nucleic acid. In some such methods, the modification cassette is at least about 200 nucleotides in length. In some such methods, the modification cassette modification cassette is a size that cannot be directly synthesized or generated by polymerase chain reaction. In some such methods, the modification cassette is at least about 10 kb in length.

In some such methods, the targeted genetic modification comprises a point mutation, a deletion, an insertion, a replacement, or a combination thereof.

Some such methods further comprise: (e) treating the targeting vector with the first nuclease agent and the second nuclease agent following the in vitro assembly in step (d) to verify that neither the first target site for the first nuclease agent nor the second target site for the second nuclease agent are present.

DEFINITIONS

Figure 1:
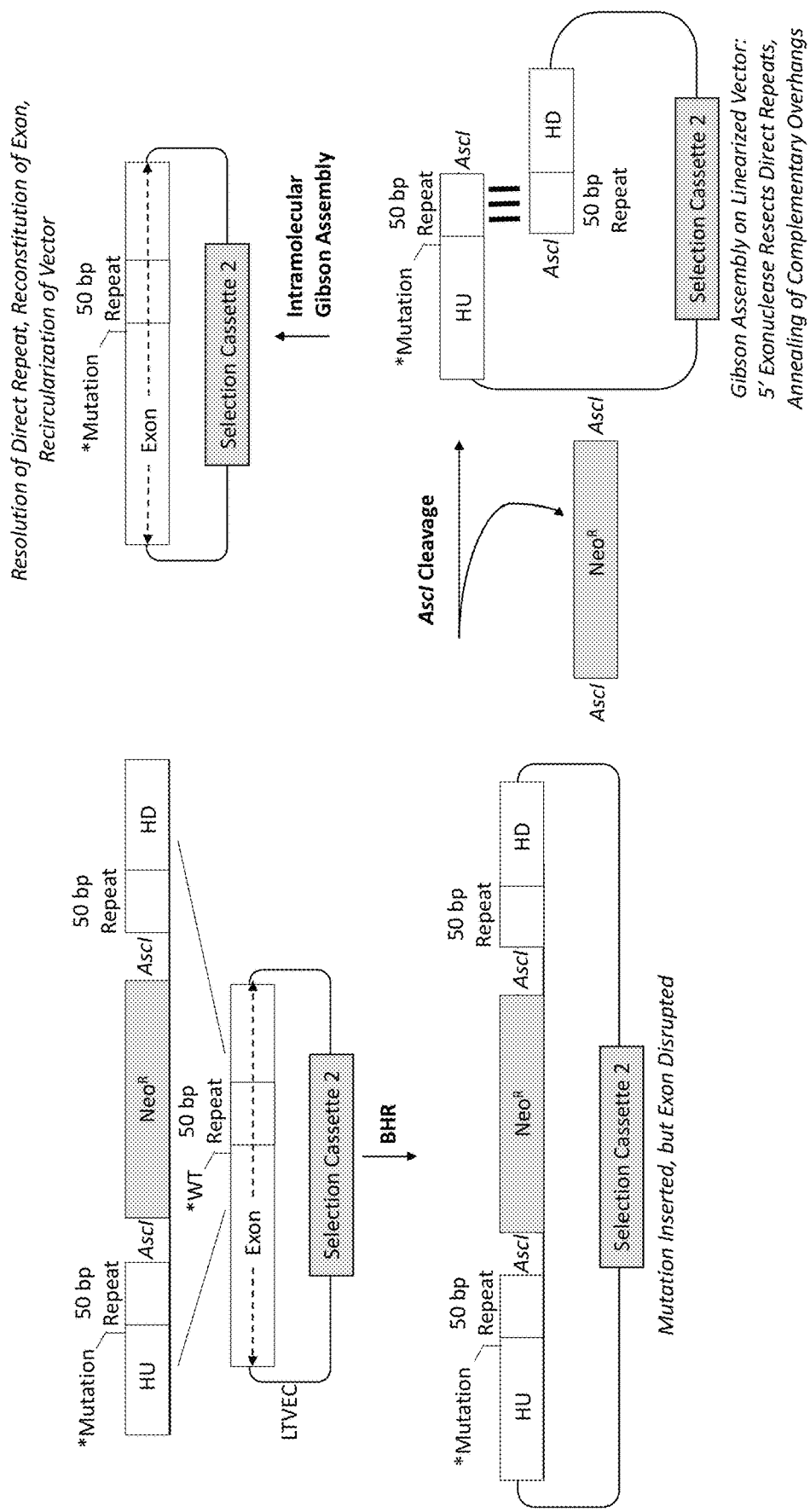
FIG. 1 (not to scale) shows a schematic of a method for scarless introduction of a point mutation into a large targeting vector via bacterial homologous recombination and intramolecular Gibson assembly.

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones. The term "domain" refers to any part of a protein or polypeptide having a particular function or structure.

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

The term "targeting vector" refers to a recombinant nucleic acid that can be introduced by homologous recombination, non-homologous-end-joining-mediated ligation, or any other means of recombination to a target position in the genome of a cell.

The term "wild type" includes entities having a structure and/or activity as found in a normal (as contrasted with mutant, diseased, altered, or so forth) state or context. Wild type genes and polypeptides often exist in multiple different forms (e.g., alleles).

The term "endogenous sequence" refers to a nucleic acid sequence that occurs naturally within a cell or non-human animal. For example, an endogenous Rosa26 sequence of a non-human animal refers to a native Rosa26 sequence that naturally occurs at the Rosa26 locus in the non-human animal.

"Exogenous" molecules or sequences include molecules or sequences that are not normally present in a cell in that form or location (e.g., genomic locus). Normal presence includes presence with respect to the particular developmental stage and environmental conditions of the cell. An exogenous molecule or sequence, for example, can include a mutated version of a corresponding endogenous sequence within the cell, such as a humanized version of the endogenous sequence, or can include a sequence corresponding to an endogenous sequence within the cell but in a different form (i.e., not within a chromosome). In contrast, endogenous molecules or sequences include molecules or sequences that are normally present in that form and location in a particular cell at a particular developmental stage under particular environmental conditions.

The term "heterologous" when used in the context of a nucleic acid or a protein indicates that the nucleic acid or protein comprises at least two segments that do not naturally occur together in the same molecule. For example, the term "heterologous," when used with reference to segments of a nucleic acid or segments of a protein, indicates that the nucleic acid or protein comprises two or more sub-sequences that are not found in the same relationship to each other (e.g., joined together) in nature. As one example, a "heterologous" region of a nucleic acid vector is a segment of nucleic acid within or attached to another nucleic acid molecule that is not found in association with the other molecule in nature. For example, a heterologous region of a nucleic acid vector could include a coding sequence flanked by sequences not found in association with the coding sequence in nature. Likewise, a "heterologous" region of a protein is a segment of amino acids within or attached to another peptide molecule that is not found in association with the other peptide molecule in nature (e.g., a fusion protein, or a protein with a tag). Similarly, a nucleic acid or protein can comprise a heterologous label or a heterologous secretion or localization sequence.

"Codon optimization" takes advantage of the degeneracy of codons, as exhibited by the multiplicity of three-base pair codon combinations that specify an amino acid, and generally includes a process of modifying a nucleic acid sequence for enhanced expression in particular host cells by replacing at least one codon of the native sequence with a codon that is more frequently or most frequently used in the genes of the host cell while maintaining the native amino acid sequence. For example, a nucleic acid encoding a Cas9 protein can be modified to substitute codons having a higher frequency of usage in a given prokaryotic or eukaryotic cell, including a bacterial cell, a yeast cell, a human cell, a non-human cell, a mammalian cell, a rodent cell, a mouse cell, a rat cell, a hamster cell, or any other host cell, as compared to the naturally occurring nucleic acid sequence. Codon usage tables are readily available, for example, at the "Codon Usage Database." These tables can be adapted in a number of ways. See Nakamura et al. (2000) *Nucleic Acids Res.* 28:292, herein incorporated by reference in its entirety for all purposes. Computer algorithms for codon optimization of a particular sequence for expression in a particular host are also available (see, e.g., Gene Forge).

The term "locus" refers to a specific location of a gene (or significant sequence), DNA sequence, polypeptide-encoding sequence, or position on a chromosome of the genome of an organism. For example, a Rosa26 locus may refer to the specific location of a Rosa26 gene, Rosa26 DNA sequence, or Rosa26 position on a chromosome of the genome of an organism that has been identified as to where such a sequence resides. A "Rosa26 locus" may comprise a regulatory element of a Rosa26 gene, including, for example, an enhancer, a promoter, 5' and/or 3' untranslated region (UTR), or a combination thereof.

The term "gene" refers to a DNA sequence in a chromosome that codes for a product (e.g., an RNA product and/or a polypeptide product) and includes the coding region interrupted with non-coding introns and sequence located adjacent to the coding region on both the 5' and 3' ends such that the gene corresponds to the full-length mRNA (including the 5' and 3' untranslated sequences). The term "gene" also includes other non-coding sequences including regulatory sequences (e.g., promoters, enhancers, and transcription factor binding sites), polyadenylation signals, internal ribosome entry sites, silencers, insulating sequence, and matrix attachment regions. These sequences may be close to the coding region of the gene (e.g., within 10 kb) or at distant sites, and they influence the level or rate of transcription and translation of the gene.

A "promoter" is a regulatory region of DNA usually comprising a TATA box capable of directing RNA polymerase II to initiate RNA synthesis at the appropriate transcription initiation site for a particular polynucleotide sequence. A promoter may additionally comprise other regions which influence the transcription initiation rate. The promoter sequences disclosed herein modulate transcription of an operably linked polynucleotide. A promoter can be active in one or more of the cell types disclosed herein (e.g., a prokaryotic cell or a eukaryotic cell (such as a mammalian cell), or a combination thereof). A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Examples of promoters can be found, for example, in WO 2013/176772, herein incorporated by reference in its entirety for all purposes.

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors. Operable linkage can include such sequences being contiguous with each other or acting in trans (e.g., a regulatory sequence can act at a distance to control transcription of the coding sequence).

"Complementarity" of nucleic acids means that a nucleotide sequence in one strand of nucleic acid, due to orientation of its nucleobase groups, forms hydrogen bonds with another sequence on an opposing nucleic acid strand. The complementary bases in DNA are typically A with T and C with G. In RNA, they are typically C with G and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm (melting temperature) of hybridized strands, or by empirical determination of Tm by using routine methods. Tm includes the temperature at which a population of hybridization complexes formed between two nucleic acid strands are 50% denatured (i.e., a population of double-stranded nucleic acid molecules becomes half dissociated into single strands). At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1M NaCl solution by using, e.g., Tm=81.5+ 0.41(% G+C), although other known Tm computations take into account nucleic acid structural characteristics.

Hybridization requires that the two nucleic acids contain complementary sequences, although mismatches between bases are possible. The conditions appropriate for hybridization between two nucleic acids depend on the length of the nucleic acids and the degree of complementation, variables which are well known. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or fewer, 30 or fewer, 25 or fewer, 22 or fewer, 20 or fewer, or 18 or fewer nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid include at least about 15 nucleotides, at least about 20 nucleotides, at least about 22 nucleotides, at least about 25 nucleotides, and at least about 30 nucleotides. Furthermore, the temperature and wash solution salt concentration may be adjusted as necessary according to factors such as length of the region of complementation and the degree of complementation.

The sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide (e.g., gRNA) can comprise at least 70%, at least 80%, at least 90%, at least 95%, at least 99%, or 100% sequence complementarity to a target region within the target nucleic acid sequence to which they are targeted. For example, a gRNA in which 18 of 20 nucleotides are complementary to a target region, and would therefore specifically hybridize, would represent 90% complementarity. In this example, the remaining noncomplementary nucleotides may be clustered or interspersed with complementary nucleotides and need not be contiguous to each other or to complementary nucleotides.

Percent complementarity between particular stretches of nucleic acid sequences within nucleic acids can be determined routinely using BLAST programs (basic local alignment search tools) and PowerBLAST programs (Altschul et al. (1990) *J. Mol. Biol.* 215:403-410; Zhang and Madden (1997) *Genome Res.* 7:649-656, each of which is herein incorporated by reference in its entirety for all purposes) or by using the Gap program (Wisconsin Sequence Analysis Package, Version 8 for Unix, Genetics Computer Group, University Research Park, Madison Wis.), using default settings, which uses the algorithm of Smith and Waterman (1981) *Adv. Appl. Math.* 2:482-489, herein incorporated by reference in its entirety for all purposes.

The methods and compositions provided herein employ a variety of different components. Some components throughout the description can have active variants and fragments. Such components include, for example, Cas proteins, CRISPR RNAs, tracrRNAs, and guide RNAs. Biological activity for each of these components is described elsewhere herein. The term "functional" refers to the innate ability of a protein or nucleic acid (or a fragment or variant thereof) to exhibit a biological activity or function. Such biological activities or functions can include, for example, the ability of a Cas protein to bind to a guide RNA and to a target DNA sequence. The biological functions of functional fragments or variants may be the same or may in fact be changed (e.g., with respect to their specificity or selectivity or efficacy) in comparison to the original, but with retention of the basic biological function.

The term "variant" refers to a nucleotide sequence differing from the sequence most prevalent in a population (e.g., by one nucleotide) or a protein sequence different from the sequence most prevalent in a population (e.g., by one amino acid).

The term "fragment" when referring to a protein means a protein that is shorter or has fewer amino acids than the full-length protein. The term "fragment" when referring to a nucleic acid means a nucleic acid that is shorter or has fewer nucleotides than the full-length nucleic acid. A fragment can be, for example, an N-terminal fragment (i.e., removal of a portion of the C-terminal end of the protein), a C-terminal fragment (i.e., removal of a portion of the N-terminal end of the protein), or an internal fragment.

"Sequence identity" or "identity" in the context of two polynucleotides or polypeptide sequences makes reference to the residues in the two sequences that are the same when aligned for maximum correspondence over a specified comparison window. When percentage of sequence identity is used in reference to proteins, residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

"Percentage of sequence identity" includes the value determined by comparing two optimally aligned sequences (greatest number of perfectly matched residues) over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise specified (e.g., the shorter sequence includes a linked heterologous sequence), the comparison window is the full length of the shorter of the two sequences being compared.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized in Table 1 below.

TABLE 1

Amino Acid Categorizations.

| Alanine | Ala | A | Nonpolar | Neutral | 1.8 |
|---|---|---|---|---|---|
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

A "homologous" sequence (e.g., nucleic acid sequence) includes a sequence that is either identical or substantially similar to a known reference sequence, such that it is, for example, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to the known reference sequence. Homologous sequences can include, for example, orthologous sequence and paralogous sequences. Homologous genes, for example, typically descend from a common ancestral DNA sequence, either through a speciation event (orthologous genes) or a genetic duplication event (paralogous genes). "Orthologous" genes include genes in different species that evolved from a common ancestral gene by speciation. Orthologs typically retain the same function in the course of evolution. "Paralogous" genes include genes related by duplication within a genome. Paralogs can evolve new functions in the course of evolution.

The term "in vitro" includes artificial environments and to processes or reactions that occur within an artificial environment (e.g., a test tube). The term "in vivo" includes natural environments (e.g., a cell or organism or body) and to processes or reactions that occur within a natural environment. The term "ex vivo" includes cells that have been removed from the body of an individual and to processes or reactions that occur within such cells.

Repair in response to double-strand breaks (DSBs) occurs principally through two conserved DNA repair pathways: homologous recombination (HR) and non-homologous end joining (NHEJ). See Kasparek & Humphrey (2011) Seminars in Cell & Dev. Biol. 22:886-897, herein incorporated by reference in its entirety for all purposes. Likewise, repair of a target nucleic acid mediated by an exogenous donor nucleic acid can include any process of exchange of genetic information between the two polynucleotides.

The term "recombination" includes any process of exchange of genetic information between two polynucleotides and can occur by any mechanism. Recombination can occur via homology directed repair (HDR) or homologous recombination (HR). HDR or HR includes a form of nucleic acid repair that can require nucleotide sequence homology, uses a "donor" molecule as a template for repair of a "target" molecule (i.e., the one that experienced the double-strand break), and leads to transfer of genetic information from the donor to target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. In some cases, the donor polynucleotide, a portion of the donor polynucleotide, a copy of the donor polynucleotide, or a portion of a copy of the donor polynucleotide integrates into the target DNA. See Wang et al. (2013) Cell 153:910-918; Mandalos et al. (2012) PLOS ONE 7:e45768:1-9; and Wang et al. (2013) Nat Biotechnol. 31:530-532, each of which is herein incorporated by reference in its entirety for all purposes.

Compositions or methods "comprising" or "including" one or more recited elements may include other elements not specifically recited. For example, a composition that "comprises" or "includes" a protein may contain the protein alone or in combination with other ingredients. The transitional phrase "consisting essentially of" means that the scope of a claim is to be interpreted to encompass the specified elements recited in the claim and those that do not materially affect the basic and novel characteristic(s) of the claimed invention. Thus, the term "consisting essentially of" when used in a claim of this invention is not intended to be interpreted to be equivalent to "comprising."

"Optional" or "optionally" means that the subsequently described event or circumstance may or may not occur and that the description includes instances in which the event or circumstance occurs and instances in which it does not.

Designation of a range of values includes all integers within or defining the range, and all subranges defined by integers within the range.

Unless otherwise apparent from the context, the term "about" encompasses values within a standard margin of error of measurement (e.g., SEM) of a stated value.

The term "and/or" refers to and encompasses any and all possible combinations of one or more of the associated listed items, as well as the lack of combinations when interpreted in the alternative ("or").

The term "or" refers to any one member of a particular list and also includes any combination of members of that list.

The singular forms of the articles "a," "an," and "the" include plural references unless the context clearly dictates otherwise. For example, the term "a protein" or "at least one protein" can include a plurality of proteins, including mixtures thereof.

Statistically significant means $p \leq 0.05$.

DETAILED DESCRIPTION

I. Overview

Provided herein are methods for introducing a scarless targeted genetic modification into a preexisting targeting vector. The methods can use combinations of bacterial homologous recombination (BHR) and in vitro assembly methods (either intramolecular or intermolecular) to introduce such targeted genetic modifications into a targeting vector in a scarless manner. The term scarless refers to the fact that no changes or undesired sequences are introduced into assembled DNA by the reactions. The combined sequence will correspond to the exact sequence desired with no changes or artefacts being introduced by the BHR or in vitro assembly procedures.

One of the most effective approaches for determining gene function involves deliberately engineering gene mutations in mouse embryonic stem (ES) cells (or other non-human animal ES cells), and then generating mice (or other non-human animals) harboring the corresponding genetic changes. The two limiting steps are the generation of gene targeting vectors and the subsequent selection of rare ES cell clones in which the targeting vector has correctly altered the gene. To produce a desired genetic alteration in ES cells, one must first introduce the alteration into a targeting vector that is subsequently used to replace the native gene in ES cells by homologous recombination.

Figure 4A:
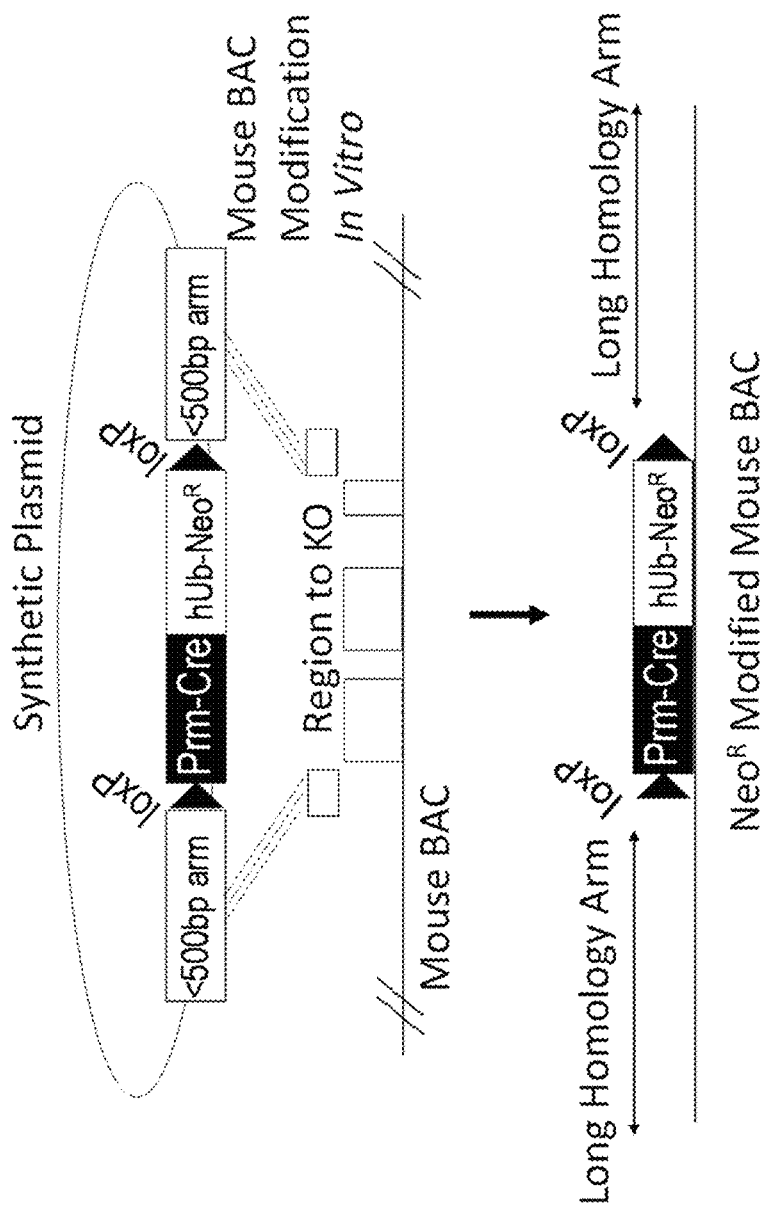
FIGS. 4A-4B show a traditional targeting strategy using modified mouse BACs as vectors and self-deleting cassette technology, from vector construction (FIG. 4A) through F1 mouse generation (FIG. 4B). Deletion of cassette via mouse protamine-expressed Cre recombinase leaves a 78 bp scar containing a single loxP.
Figure 4B:
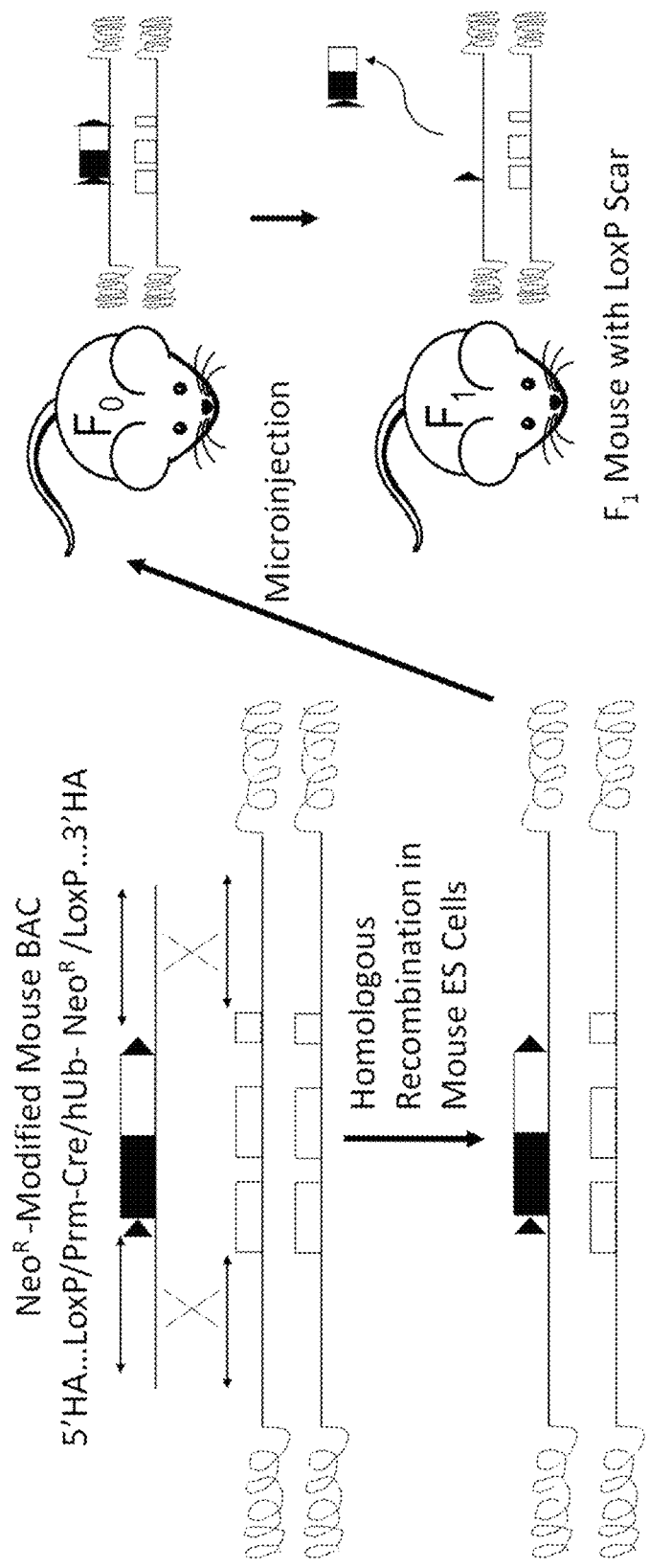

Scarless DNA construction is of particular importance when creating transgenic animal lines, as the scars produced by restriction sites or other manipulations can negatively impact gene expression if they land in a region important for regulation. Targeting the mammalian genome often requires construction of large targeting vectors with long DNA arms to direct homologous recombination, as well as antibiotic resistance cassettes for selection of embryonic stem cell clones. Correctly targeted clones often contain multiple scars necessary for construction of the vector and the resistance cassette itself. Even with self-deleting cassette technology, it is often not possible to avoid leaving exogenous sequence "scars" behind in modified loci. See, e.g., FIGS. 4A-4B. Such scars can affect faithful expression of the targeted locus or even the expression of neighboring genes. As animal models become more complex, more modifications may be added on top of existing ones, such as human disease-causing mutations on humanized alleles. The additional changes can then add even more scars and another selection cassette to an already highly engineered mouse locus, increasing the likelihood that expression will be altered and the mouse model will not be faithful. In addition, adding a new cassette to a vector already containing one can become complicated due to undesired recombination between shared cassette elements such as promoters and poly(A) signals, even if the two cassettes encode different selections. However, such selection cassettes are important so that time and resources do not have to be wasted screening thousands of ES cell clones for a desired modification.

Alternatively, using the initial targeting vector to create and screen modified ES cells comprising the modification from the initial targeting vector and then re-targeting those cells with a second targeting vector (e.g., ssODN) to make a second modification to the already targeted locus is time-consuming, and re-targeting (e.g., with ssODNs) can lead to undesired modifications such as undesired insertions, undesired deletions, undesired point mutation, or no targeting coupled with a transgenic insertion elsewhere in the genome.

The methods disclosed herein provide efficient and scarless methods for making modifications to preexisting targeting vectors at the stage of preparing the targeting vector instead of having to create and screen ES cells comprising the initial preexisting targeting vector, and then re-targeting those cells to make a second modification to the already targeted locus.

II. Scarless Introduction of a Targeted Modification into a Targeting Vector Via Bacterial Homologous Recombination and Intramolecular In Vitro Assembly Some methods disclosed herein for scarless introduction of a targeted genetic modification into a preexisting targeting vector take advantages of in vitro assembly methods for intramolecular assembly. As one example, such methods can comprise performing bacterial homologous recombination between the preexisting targeting vector and a modification cassette in a population of bacterial cells. The modification cassette can comprise an insert nucleic acid flanked by a 5' homology arm corresponding to a 5' target sequence in the preexisting targeting vector and a 3' homology arm corresponding to a 3' target sequence in the preexisting vector. The insert nucleic acid can comprise a selection cassette flanked by target sites for one or more nuclease agents (e.g., rare-cutting nuclease agents) and repeat sequences. For example, the insert nucleic acid can comprise from 5' to 3': (1) a first repeat sequence; (2) a first target site for a first nuclease agent; (3) a selection cassette; (4) a second target site for a second nuclease agent; and (5) a second repeat sequence.

The preexisting targeting vector can be any type of targeting vector of any size. In a specific example, the preexisting targeting vector is a large targeting vector (LTVEC) that is at least about 10 kb in length. In another example, it is at least about 100 kb in length. Targeting vectors and large targeting vectors are discussed in more detail elsewhere herein.

The modification cassette can be a linear nucleic acid or a circular nucleic acid, it can be a single-stranded nucleic acid or a double-stranded nucleic acid, and it can comprise deoxyribonucleic acid (DNA) or ribonucleic acid (RNA). In one specific example, the modification cassette is a linear, double-stranded DNA.

The homology arms in the modification cassette are referred to herein as 5' and 3' (i.e., upstream and downstream) homology arms. This terminology relates to the relative position of the homology arms to the nucleic acid insert within modification cassette. The 5' and 3' homology arms correspond to regions within the preexisting targeting vector to be modified, which are referred to herein as "5' target sequence" and "3' target sequence," respectively.

A homology arm and a target sequence "correspond" or are "corresponding" to one another when the two regions share a sufficient level of sequence identity to one another to act as substrates for a homologous recombination reaction (e.g., bacterial homologous recombination). The term "homology" includes DNA sequences that are either identical or share sequence identity to a corresponding sequence. The sequence identity between a given target sequence and the corresponding homology arm found in the exogenous repair template can be any degree of sequence identity that allows for homologous recombination to occur. For example, the amount of sequence identity shared by the homology arm of the exogenous repair template (or a fragment thereof) and the target sequence (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a corresponding region of homology between the homology arm and the corresponding target sequence can be of any length that is sufficient to promote homologous recombination. For example, the homology arms can be any size suitable for bacterial homologous recombination. For example, the homology arms can be at least about 35 nucleotides, at least about 40 nucleotides, at least about 50 nucleotides, at least about 60 nucleotides, at least about 70 nucleotides, at least about 80 nucleotides, at least about 90 nucleotides, at least about 100 nucleotides. For example, the homology arms can be between about 35 nucleotides and 500 nucleotides, between about 75 nucleotides and about 500 nucleotides, or between about 50 nucleotides and about 200 nucleotides (e.g., about 100 nucleotides). As another example, homology arms can be between about 35 nucleotides to about 2.5 kb in length, are between about 35 nucleotides to about 1.5 kb in length, or are between about 35 to about 500 nucleotides in length. For example, a given homology arm (or each of the homology arms) and/or corresponding target sequence can comprise corresponding regions of homology that are between about 35 to about 40, about 40 to about 50, about 50 to about 60, about 60 to about 70, about 70 to about 80, about 80 to about 90, about 90 to about 100, about 100 to about 150, about 150 to about 200, about 200 to about 250, about 250 to about 300, about 300 to about 350, about 350 to about 400, about 400 to about 450, or about 450 to about 500 nucleotides in length, such that the homology arms have sufficient homology to undergo homologous recombination with the corresponding target sequences within the target nucleic acid. Alternatively, a given homology arm (or each homology arm) and/or corresponding target sequence can comprise corresponding regions of homology that are between about 0.5 kb to about 1 kb, about 1 kb to about 1.5 kb, about 1.5 kb to about 2 kb, or about 2 kb to about 2.5 kb in length. For example, the homology arms can each be about 100 nucleotides in length. The homology arms can be symmetrical (each about the same size in length), or they can be asymmetrical (one longer than the other).

The modification cassette can be of any length. For example, a modification cassette can be from about 10 kb to about 400 kb, from about 20 kb to about 400 kb, from about 20 kb to about 30 kb, from about 30 kb to about 40 kb, from about 40 kb to about 50 kb, from about 50 kb to about 75 kb, from about 75 kb to about 100 kb, from about 100 kb to 125 kb, from about 125 kb to about 150 kb, from about 150 kb to about 175 kb, about 175 kb to about 200 kb, from about 200 kb to about 225 kb, from about 225 kb to about 250 kb, from about 250 kb to about 275 kb or from about 275 kb to about 300 kb, from about 200 kb to about 300 kb, from about 300 kb to about 350 kb, or from about 350 kb to about 400 kb. In one example, a modification cassette can be at least about 100 kb or 100 kb in length. A modification cassette can also be from about 50 kb to about 500 kb, from about 100 kb to about 125 kb, from about 300 kb to about 325 kb, from about 325 kb to about 350 kb, from about 350 kb to about 375 kb, from about 375 kb to about 400 kb, from about 400 kb to about 425 kb, from about 425 kb to about 450 kb, from about 450 kb to about 475 kb, or from about 475 kb to about 500 kb. Alternatively, a modification cassette can be at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, at least 300 kb, at least 350 kb, at least 400 kb, at least 450 kb, or at least 500 kb or greater. In one example, the modification cassette is between about 1 kb and about 15 kb in length or between about 1 kb and about 10 kb in length (e.g., about 1.2 kb, about 5 kb, about 8 kb, or about 15 kb).

The modification cassette can comprise the targeted genetic modification. For example, the targeted genetic modification can be in the 5' homology arm or the 3' homology arm (e.g., a small modification such as a point mutation or a small deletion, insertion, or replacement that will not negatively affect the ability of the homology arm to recombine with the target sequence). Alternatively, the targeted genetic modification can be in the insert nucleic acid (e.g., when the targeted genetic modification is an insertion or a replacement). If the only targeted genetic modification is a deletion, then the 5' homology arm and 3' homology arm can be designed to target 5' and 3' target sequences, respectively, that flank the sequence targeted for deletion in the preexisting targeting vector. As one example, the targeted genetic modification can be in the first repeat sequence and/or in the second repeat sequence in the insert nucleic acid. Types of possible targeted genetic modifications are disclosed in more detail elsewhere herein. Some examples include point mutations, deletions, insertions, replacements, or combinations thereof.

The first and second repeat sequences in the modification cassette can be identical to each other. The repeat sequence can be identical to a sequence in the preexisting targeting vector. Alternatively, in the case that the targeted genetic modification comprises an insertion (e.g., an insertion alone, or an insertion in combination with a deletion (i.e., replacement)), the repeat sequence can be identical to the 5' end or the 3' end of the insertion.

The repeat sequence can be of any suitable size for subsequent assembly between the first and second repeat sequences in an in vitro assembly reaction. As one example, the repeat sequence can comprise at least about 20 nucleotides, at least about 30 nucleotides, at least about 40 nucleotides, or at least about 50 nucleotides. As another example, the repeat sequence can have a length of between about 20 nucleotides and about 100 nucleotides, between about 20 nucleotides and about 90 nucleotides, between about 0 nucleotides and about 80 nucleotides, between about 20 nucleotides and about 70 nucleotides, between about 20 nucleotides and about 60 nucleotide, between about 20 nucleotides and about 50 nucleotides, between about 20 nucleotides and about 40 nucleotides, between about 30 nucleotides and about 60 nucleotides, or between about 40 nucleotides and about 50 nucleotides. In a specific example, the repeat sequence can have a length of between about 40 nucleotides and about 50 nucleotides (e.g., about 40 nucleotides or about 50 nucleotides).

Following bacterial homologous recombination, bacterial cells comprising a modified targeting vector comprising the selection cassette (and comprising the targeted genetic modification) can be selected. Examples of selection cassettes and selection methods are disclosed in more detail elsewhere herein. In a specific example, the selection cassette imparts resistance to an antibiotic. For example, it can impart resistance to any one of ampicillin, chloramphenicol, tetracycline, kanamycin, spectinomycin, streptomycin, carbenicillin, bleomycin, erythromycin, or polymyxin B. In some methods, the preexisting targeting vector also comprises a second selection cassette. The second selection cassette can, for example, also impart resistance to an antibiotic. The selection cassette in the modification cassette and the second selection cassette in the preexisting targeting vector can each impart resistance to a different antibiotic. For example, the selection cassette in the modification cassette can impart resistance to a first antibiotic, and the second selection cassette in the preexisting targeting vector can impart resistance to a second, different antibiotic. In some methods, the second selection cassette can allow for selection in both bacterial cells and eukaryotic or mammalian cells.

Following selection, the first target site in the modified targeting vector can be cleaved with the first nuclease agent, and the second target site in the modified targeting vector can be cleaved with the second nuclease agent to remove the selection cassette and expose the first repeat sequence and the second repeat sequence in the modified targeting vector. For example, this step can be done in vitro. As an example, DNA can be isolated from the bacterial cells following bacterial homologous recombination and selection, after which the first target site in the modified targeting vector can be cleaved with the first nuclease agent in vitro, and the second target site in the modified targeting vector can be cleaved with the second nuclease agent in vitro to remove the selection cassette and expose the first repeat sequence and the second repeat sequence in the modified targeting vector.

The first nuclease agent and/or the second nuclease agent can be a rare-cutting nuclease agent as described elsewhere herein. For example, in some methods, the first target site and/or the second target site are not present in the preexisting targeting vector. The first and second target sites can be different, or the first target site can be identical to the second target site, and the first nuclease agent can be identical to the second nuclease agent. The first nuclease agent and/or the second nuclease agent can create a blunt end, a 5' overhang, or a 3' overhang. In one example, the first nuclease agent and/or the second nuclease agent creates a 3' overhang.

In one specific example, the first nuclease agent and/or the second nuclease agent is a restriction enzyme or a rare-cutting restriction enzyme. Examples of rare-cutting restriction enzymes are disclosed elsewhere herein but can include, for example, NotI, XmaIII, SstII, SalI, NruI, NheI, Nb.BbvCI, BbvCI, AscI, AsiSI, FseI, PacI, PmeI, SbfI, SgrAI, SwaI, BspQI, SapI, SfiI, CspCI, AbsI, CciNI, FspAI, MauBI, MreI, MssI, PalAI, RgaI, RigI, SdaI, SfaAI, SgfI, SgrDI, SgsI, SmiI, SrfI, Sse2321, Sse83871, LguI, PciSI, AarI, AjuI, AloI, BarI, PpiI, and PsrI.

In another specific example, the first nuclease agent and/or the second nuclease agent can be an engineered nuclease agent. For example, the nuclease agent can be a Clustered Regularly Interspaced Short Palindromic Repeats (CRISPR)-associated (Cas) protein and a guide RNA (gRNA) (e.g., Cas9 and a gRNA comprising a CRISPR RNA (crRNA) and a trans-activating CRISPR RNA (tracrRNA)), a zinc finger nuclease (ZFN), a Transcription Activator-Like Effector Nuclease (TALEN), or an engineered meganuclease Following cleavage/digestion, the exposed first repeat sequence can be assembled with the exposed second repeat sequence in an intramolecular in vitro assembly reaction to generate the targeting vector comprising the scarless targeted genetic modification. For example, in some such methods, neither the first target site for the first nuclease agent nor the second target site for the second nuclease agent are present in the targeting vector comprising the scarless targeted genetic modification (i.e., following in vitro assembly). Likewise, in some such methods, only a single copy of the repeat sequence is present in the targeting vector comprising the scarless targeted genetic modification (i.e., following in vitro assembly).

Any suitable in vitro assembly method can be used. In one specific example, the in vitro assembly step can comprise incubating the modified targeting vector with an exonuclease, a DNA polymerase, and a DNA ligase. For example, the in vitro assembly method can comprise contacting the modified targeting vector with an exonuclease to expose complementary sequences between the first repeat sequence and the second repeat sequence, annealing the exposed complementary sequences, extending the 3' ends of the annealed complementary sequences, and ligating the annealed complementary sequences. Examples of in vitro assembly methods are discussed in more detail elsewhere herein.

In some methods, to reduce background, the vector produced by the in vitro assembly can be treated with the first nuclease agent and/or the second nuclease agent to reduce background (e.g., by cleaving any targeting vectors that did not successfully assemble and therefore still contain the target site for the first nuclease agent or the second nuclease agent). Such a step can help verify that neither the first target site for the first nuclease agent nor the second target site for the second nuclease agent are present.

III. Scarless Introduction of a Targeted Modification into a Targeting Vector Via Bacterial Homologous Recombination and Intermolecular In Vitro Assembly Other methods disclosed herein for scarless introduction of a targeted genetic modification into a preexisting targeting vector take advantage of in vitro assembly methods for intermolecular assembly. As one example, such methods can comprise performing bacterial homologous recombination between the preexisting targeting vector and a deletion cassette in a population of bacterial cells. The deletion cassette can comprise an insert nucleic acid flanked by a 5' homology arm corresponding to a 5' target sequence in the preexisting targeting vector and a 3' homology arm corresponding to a 3' target sequence in the preexisting vector. The 5' target sequence and the 3' target sequence clan flank a region of the preexisting targeting vector into which the targeted genetic modification is to be introduced. The insert nucleic acid can comprise a selection cassette flanked by target sites for one or more nuclease agents (e.g., rare-cutting nuclease agents). For example, the insert nucleic acid can comprise from 5' to 3': (1) a first target site for a first nuclease agent; (2) a selection cassette; and (3) a second target site for a second nuclease agent.

The preexisting targeting vector can be any type of targeting vector of any size. In a specific example, the preexisting targeting vector is a large targeting vector (LTVEC) that is at least about 10 kb in length. In another example, it is at least about 100 kb in length. Targeting vectors are discussed in more detail elsewhere herein.

The deletion cassette can be a linear nucleic acid or a circular nucleic acid, it can be a single-stranded nucleic acid or a double-stranded nucleic acid, and it can comprise deoxyribonucleic acid (DNA) or ribonucleic acid (RNA). In one specific example, the modification cassette is a linear, double-stranded DNA.

The homology arms in the deletion cassette are referred to herein as 5' and 3' (i.e., upstream and downstream) homology arms. This terminology relates to the relative position of the homology arms to the nucleic acid insert within deletion cassette. The 5' and 3' homology arms correspond to regions within the preexisting targeting vector to be modified, which are referred to herein as "5' target sequence" and "3' target sequence," respectively.

A homology arm and a target sequence "correspond" or are "corresponding" to one another when the two regions share a sufficient level of sequence identity to one another to act as substrates for a homologous recombination reaction (e.g., bacterial homologous recombination). The term "homology" includes DNA sequences that are either identical or share sequence identity to a corresponding sequence. The sequence identity between a given target sequence and the corresponding homology arm found in the exogenous repair template can be any degree of sequence identity that allows for homologous recombination to occur. For example, the amount of sequence identity shared by the homology arm of the exogenous repair template (or a fragment thereof) and the target sequence (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a corresponding region of homology between the homology arm and the corresponding target sequence can be of any length that is sufficient to promote homologous recombination. For example, the homology arms can be any size suitable for bacterial homologous recombination. For example, the homology arms can be at least about 35 nucleotides, at least about 40 nucleotides, at least about 50 nucleotides, at least about 60 nucleotides, at least about 70 nucleotides, at least about 80 nucleotides, at least about 90 nucleotides, at least about 100 nucleotides. For example, the homology arms can be between about 35 nucleotides and 500 nucleotides, between about 75 nucleotides and about 500 nucleotides, or between about 50 nucleotides and about 200 nucleotides (e.g., about 100 nucleotides). As another example, homology arms can be between about 35 nucleotides to about 2.5 kb in length, are between about 35 nucleotides to about 1.5 kb in length, or are between about 35 to about 500 nucleotides in length. For example, a given homology arm (or each of the homology arms) and/or corresponding target sequence can comprise corresponding regions of homology that are between about 35 to about 40, about 40 to about 50, about 50 to about 60, about 60 to about 70, about 70 to about 80, about 80 to about 90, about 90 to about 100, about 100 to about 150, about 150 to about 200, about 200 to about 250, about 250 to about 300, about 300 to about 350, about 350 to about 400, about 400 to about 450, or about 450 to about 500 nucleotides in length, such that the homology arms have sufficient homology to undergo homologous recombination with the corresponding target sequences within the target nucleic acid. Alternatively, a given homology arm (or each homology arm) and/or corresponding target sequence can comprise corresponding regions of homology that are between about 0.5 kb to about 1 kb, about 1 kb to about 1.5 kb, about 1.5 kb to about 2 kb, or about 2 kb to about 2.5 kb in length. For example, the homology arms can each be about 100 nucleotides in length. The homology arms can be symmetrical (each about the same size in length), or they can be asymmetrical (one longer than the other).

The deletion cassette can be of any length. For example, a deletion cassette can be from about 10 kb to about 400 kb, from about 20 kb to about 400 kb, from about 20 kb to about 30 kb, from about 30 kb to about 40 kb, from about 40 kb to about 50 kb, from about 50 kb to about 75 kb, from about 75 kb to about 100 kb, from about 100 kb to about 125 kb, from about 125 kb to about 150 kb, from about 150 kb to about 175 kb, about 175 kb to about 200 kb, from about 200 kb to about 225 kb, about 225 kb to about 250 kb, from about 250 kb to about 275 kb or from about 275 kb to about 300 kb, from about 200 kb to about 300 kb, from about 300 kb to about 350 kb, or from about 350 kb to about 400 kb. In one example, a deletion cassette can be at least about 100 kb or 100 kb in length. A deletion cassette can also be from about 50 kb to about 500 kb, from about 100 kb to about 125 kb, from about 300 kb to about 325 kb, from about 325 kb to about 350 kb, from about 350 kb to about 375 kb, from about 375 kb to about 400 kb, from about 400 kb to about 425 kb, from about 425 kb to about 450 kb, from about 450 kb to about 475 kb, or from about 475 kb to about 500 kb. Alternatively, a deletion cassette can be at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, at least 300 kb, at least 350 kb, at least 400 kb, at least 450 kb, or at least 500 kb or greater. In one example, the deletion cassette is between about 1 kb and about 15 kb in length or between about 1 kb and about 10 kb in length (e.g., about 1.2 kb, about 5 kb, about 8 kb, or about 15 kb).

Following bacterial homologous recombination, bacterial cells comprising a modified targeting vector comprising the selection cassette can be selected. Examples of selection cassettes and selection methods are disclosed in more detail elsewhere herein. In a specific example, the selection cassette imparts resistance to an antibiotic. For example, it can impart resistance to any one of ampicillin, chloramphenicol, tetracycline, kanamycin, spectinomycin, streptomycin, carbenicillin, bleomycin, erythromycin, or polymyxin B. In some methods, the preexisting targeting vector also comprises a second selection cassette. The second selection cassette can, for example, also impart resistance to an antibiotic. The selection cassette in the deletion cassette and the second selection cassette in the preexisting targeting vector can each impart resistance to a different antibiotic. For example, the selection cassette in the deletion cassette can impart resistance to a first antibiotic, and the second selection cassette in the preexisting targeting vector can impart resistance to a second, different antibiotic. In some methods, the second selection cassette can allow for selection in both bacterial cells and eukaryotic or mammalian cells.

Following selection, the first target site in the modified targeting vector can be cleaved with the first nuclease agent, and the second target site in the modified targeting vector can be cleaved with the second nuclease agent to remove the selection cassette and expose an upstream end sequence and a downstream end sequence in the modified targeting vector. For example, this step can be done in vitro. As an example, DNA can be isolated from the bacterial cells following bacterial homologous recombination and selection, after which the first target site in the modified targeting vector can be cleaved with the first nuclease agent in vitro, and the second target site in the modified targeting vector can be cleaved with the second nuclease agent in vitro to remove the selection cassette and expose the upstream end sequence and the downstream end sequence in the modified targeting vector.

The first nuclease agent and/or the second nuclease agent can be a rare-cutting nuclease agent as described elsewhere herein. For example, in some methods, the first target site and/or the second target site are not present in the preexisting targeting vector. The first and second target sites can be different, or the first target site can be identical to the second target site, and the first nuclease agent can be identical to the second nuclease agent. The first nuclease agent and/or the second nuclease agent can create a blunt end, a 5' overhang, or a 3' overhang. In one example, the first nuclease agent and/or the second nuclease agent creates a 3' overhang.

In one specific example, the first nuclease agent and/or the second nuclease agent is a restriction enzyme or a rare-cutting restriction enzyme. Examples of rare-cutting restriction enzymes are disclosed elsewhere herein but can include, for example, NotI, XmaIII, SstII, SalI, NruI, NheI, Nb.BbvCI, BbvCI, AscI, AsiSI, FseI, PacI, PmeI, SbfI, SgrAI, SwaI, BspQI, SapI, SfiI, CspCI, AbsI, CciNI, FspAI, MauBI, MreI, MssI, PalAI, RgaI, RigI, SdaI, SfaAI, SgfI, SgrDI, SgsI, SmiI, SrfI, Sse2321, Sse8387I, LguI, PciSI, AarI, AjuI, AloI, BarI, PpiI, and PsrI.

In another specific example, the first nuclease agent and/or the second nuclease agent can be an engineered nuclease agent. For example, the nuclease agent can be a Clustered Regularly Interspaced Short Palindromic Repeats (CRISPR)-associated (Cas) protein and a guide RNA (gRNA) (e.g., Cas9 and a gRNA comprising a CRISPR RNA (crRNA) and a trans-activating CRISPR RNA (tracrRNA)), a zinc finger nuclease (ZFN), a Transcription Activator-Like Effector Nuclease (TALEN), or an engineered meganuclease Following cleavage/digestion, the cleaved targeting vector can be assembled in an in vitro intermolecular assembly reaction with a modification cassette comprising the targeted genetic modification flanked by an upstream end sequence overlapping the upstream end sequence in the modified targeting vector and a downstream end sequence overlapping the downstream end sequence in the modified targeting vector to generate the targeting vector comprising the scarless targeted genetic modification. For example, in some such methods, neither the first target site for the first nuclease agent nor the second target site for the second nuclease agent are present in the targeting vector comprising the scarless targeted genetic modification.

Any suitable in vitro assembly method can be used. In one specific example, the in vitro assembly step can comprise incubating the cleaved targeting vector and the modification cassette with an exonuclease, a DNA polymerase, and a DNA ligase. For example, the in vitro assembly method can comprise contacting the cleaved targeting vector and the modification cassette with an exonuclease to expose complementary sequences between the end sequences in the modified targeting vector and the end sequences in the modification cassette, annealing the exposed complementary sequences, extending the 3' ends of the annealed complementary sequences, and ligating the annealed complementary sequences.

The modification cassette can be a linear nucleic acid or a circular nucleic acid, it can be a single-stranded nucleic acid or a double-stranded nucleic acid, and it can comprise deoxyribonucleic acid (DNA) or ribonucleic acid (RNA). In one specific example, the modification cassette is a linear, double-stranded DNA.

The modification cassette can be of any length. For example, a modification cassette can be from about 10 kb to about 400 kb, from about 20 kb to about 400 kb, from about 20 kb to about 30 kb, from about 30 kb to about 40 kb, from about 40 kb to about 50 kb, from about 50 kb to about 75 kb, from about 75 kb to about 100 kb, from about 100 kb to 125 kb, from about 125 kb to about 150 kb, from about 150 kb to about 175 kb, about 175 kb to about 200 kb, from about 200 kb to about 225 kb, from about 225 kb to about 250 kb, from about 250 kb to about 275 kb or from about 275 kb to about 300 kb, from about 200 kb to about 300 kb, from about 300 kb to about 350 kb, or from about 350 kb to about 400 kb. In one example, a modification cassette can be at least about 100 kb or 100 kb in length. A modification cassette can also be from about 50 kb to about 500 kb, from about 100 kb to about 125 kb, from about 300 kb to about 325 kb, from about 325 kb to about 350 kb, from about 350 kb to about 375 kb, from about 375 kb to about 400 kb, from about 400 kb to about 425 kb, from about 425 kb to about 450 kb, from about 450 kb to about 475 kb, or from about 475 kb to about 500 kb. Alternatively, a modification cassette can be at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, at least 300 kb, at least 350 kb, at least 400 kb, at least 450 kb, or at least 500 kb or greater. In one specific example, the modification cassette is between about 400 bp and about 2 kb in length. In another example, the modification cassette is between about 1 kb and about 15 kb in length or between about 1 kb and about 10 kb in length (e.g., about 1.2 kb, about 5 kb, about 8 kb, or about 15 kb). In a specific example, the modification cassette is at least about 200 nucleotides in length. In another specific example, the modification cassette is a size that cannot be directly synthesized or generated by polymerase chain reaction. For example, the modification cassette can be at least about 5 kb, at least about 10 kb, at least about 15 kb, at least about 20 kb, at least about 25 kb, or at least about 30 kb in length.

The length of overlap between the upstream end sequence in the modification cassette and the upstream end sequence in the modified targeting vector and/or the length of the overlap between the downstream end sequence in the modification cassette and the downstream end sequence in the modified targeting vector can be any suitable length for an in vitro assembly reaction. As one example, the length of overlap can comprise at least about 20 nucleotides, at least about 30 nucleotides, at least about 40 nucleotides, or at least about 50 nucleotides. As another example, the length of overlap can be between about 20 nucleotides and about 100 nucleotides, between about 20 nucleotides and about 90 nucleotides, between about 0 nucleotides and about 80 nucleotides, between about 20 nucleotides and about 70 nucleotides, between about 20 nucleotides and about 60 nucleotide, between about 20 nucleotides and about 50 nucleotides, between about 20 nucleotides and about 40 nucleotides, between about 30 nucleotides and about 60 nucleotides, or between about 40 nucleotides and about 50 nucleotides. In a specific example, the length of overlap can be between about 40 nucleotides and about 50 nucleotides (e.g., about 40 nucleotides or about 50 nucleotides).

The modification cassette can comprise the targeted genetic modification. Types of targeted genetic modifications are disclosed in more detail elsewhere herein. Some examples include point mutations, deletions, insertions, replacements, or combinations thereof.

In some methods, to reduce background, the vector produced by the in vitro assembly can be treated with the first nuclease agent and/or the second nuclease agent to reduce background (e.g., by cleaving any targeting vectors that did not successfully assemble and therefore still contained the target site for the first nuclease agent or the second nuclease agent). Such a step can help verify that neither the first target site for the first nuclease agent nor the second target site for the second nuclease agent are present.

IV. Bacterial Homologous Recombination

Any suitable bacterial homologous recombination (BHR) method can be used in the methods disclosed herein. Bacterial homologous recombination involves the transient and controlled expression of genes that mediate homologous recombination in bacterial cells such as *Escherichia coli*, thereby allowing the bacteria to mediate recombination between a modification cassette and a targeting vector (e.g., large targeting vector) sharing short homologous stretches. See, e.g., US 2004/0018626 and Valenzuela et al. (2003) *Nat. Biotechnol.* 21(6):652-659, each of which is herein incorporated by reference in its entirety.

The short homologous stretches can comprise an upstream homology region and a downstream homology region. The homology regions can be any size suitable for bacterial homologous recombination. For example, the homology regions can be any size suitable for bacterial homologous recombination. For example, the homology regions can be at least about 35 nucleotides, at least about 40 nucleotides, at least about 50 nucleotides, at least about 60 nucleotides, at least about 70 nucleotides, at least about 80 nucleotides, at least about 90 nucleotides, at least about 100 nucleotides. For example, the homology regions can be between about 35 nucleotides and 500 nucleotides, between about 75 nucleotides and about 500 nucleotides, or between about 50 nucleotides and about 200 nucleotides (e.g., about 100 nucleotides). As another example, homology regions can be between about 35 nucleotides to about 2.5 kb in length, are between about 35 nucleotides to about 1.5 kb in length, or are between about 35 to about 500 nucleotides in length. For example, a homology region can be between about 35 to about 40, about 40 to about 50, about 50 to about 60, about 60 to about 70, about 70 to about 80, about 80 to about 90, about 90 to about 100, about 100 to about 150, about 150 to about 200, about 200 to about 250, about 250 to about 300, about 300 to about 350, about 350 to about 400, about 400 to about 450, or about 450 to about 500 nucleotides in length. Alternatively, a given homology region can be between about 0.5 kb to about 1 kb, about 1 kb to about 1.5 kb, about 1.5 kb to about 2 kb, or about 2 kb to about 2.5 kb in length. For example, the homology region can be about 100 nucleotides in length.

The technique of modifying a targeting vector using bacterial homologous recombination can be performed in a variety of systems (see, e.g., Yang et al. (1997) *Nat. Biotechnol.* 15:859-65; Muyrers et al. (1999) *Nucleic Acids Res.* 27:1555-1557; Angrand et al. (1999) *Nucleic Acids Res.*, 27:e16; Narayanan et al. (1999) *Gene Ther.*, 6:442-447; and Yu et al. (2000) *Proc. Natl. Acad. Sci. U.S.A.* 97:5978-5983, each of which is herein incorporated by reference in its entirety for all purposes). One example is ET cloning (Zhang et al. (1998) *Nat. Genet.* 20:123-128 and Narayanan et al. (1999) *Gene Ther.*, 6:442-447, each of which is herein incorporated by reference in its entirety for all purposes) and variations of this technology (Yu et al. (2000) *Proc. Natl. Acad. Sci. U.S.A.* 97:5978-5983, herein incorporated by reference in its entirety for all purposes). ET refers to the recE and recT proteins that carry out the homologous recombination reaction. RecE is an exonuclease that trims one strand of linear double-stranded DNA 5' to 3', thus leaving behind a linear double-stranded fragment with a 3' single-stranded overhang. This single-stranded overhang is coated by recT protein, which has single-stranded DNA (ssDNA) binding activity. ET cloning is performed using *E. coli* that transiently express the *E. coli* gene products of recE and recT and the bacteriophage lambda (λ) protein λgam. The λgam protein is required for protecting the donor DNA fragment from degradation by the recBC exonuclease system and it is required for efficient ET-cloning in recBC$^+$ hosts such as the frequently used *E. coli* strain DH10b.

V. In Vitro Assembly

Any in vitro assembly method that can be used to assemble at least two nucleic acid or at least two ends of a single nucleic acid under conditions effective to join the DNA molecules to form a substantially intact DNA molecule can be used in the methods described herein. Some non-limiting examples of in vitro assembly methods include standard assembly using restriction enzymes, in-fusion assembly, sequence and ligase independent cloning (SLIC), Gibson assembly, and Golden Gate assembly. See, e.g., Lee at al. (2013) *Mol. Cells* 35:359-370, herein incorporated by reference in its entirety for all purposes.

One example of a suitable in vitro assembly method is an isothermal, single-reaction method for assembling overlapping DNA molecules by the concerted action of an exonuclease (e.g., a 5' exonuclease), a DNA polymerase, and a DNA ligase. Nucleic acids having overlapping ends (or a single, linear nucleic acid with overlapping ends) can be combined with a ligase, an exonuclease, and a DNA polymerase. For example, two adjacent DNA fragments sharing terminal sequence overlaps can be joined into a covalently sealed molecule in a one-step isothermal reaction. In a specific example, two or more DNA molecules to be assembled can be contacted in vitro in a single vessel with: (a) an isolated non-thermostable 5'-to-3' exonuclease that lacks 3' exonuclease activity (e.g., a non-processive exonuclease that chews back the ends of the double-stranded DNA molecules to expose single-stranded overhangs comprising the regions of overlap); (b) a crowding agent (which, among other functions, can accelerate nucleic acid annealing, so that the single-stranded overhangs are annealed (hybridized) specifically); (c) an isolated thermostable non-strand-displacing DNA polymerase with 3' exonuclease activity, or a mixture of said DNA polymerase with a second DNA polymerase that lacks 3' exonuclease activity (to fill in remaining single-stranded gaps in the annealed molecules, by extending the 3' ends of the annealed regions); (d) an isolated thermostable ligase (which seals (ligates) the nicks thus formed); (e) a mixture of dNTPs; and (f) a suitable buffer under conditions that are effective for joining the two or more DNA molecules to form a first assembled dsDNA molecule in a one-step reaction. For single-stranded molecules, the exonuclease may be, but need not be, omitted. In a specific example, T5 exonuclease removes nucleotides from the 5' ends of the double-stranded DNA molecules, complementary single-stranded DNA overhangs are annealed, and Phusion DNA polymerase fills the gaps, and Taq DNA ligase seals the nicks. See, e.g., US 2010/0035768, US 2015/0376628, WO 2015/200334, and Gibson et al. (2009) Nat. Methods 6(5):343-345, each of which is herein incorporated by reference in its entirety for all purposes.

First and second single stranded nucleic acids have overlapping ends when their respective ends are complementary to one another. First and second double stranded nucleic acids have overlapping ends when a 5' end of a strand of the first nucleic acid is complementary to the 3' end of a strand of the second nucleic acid and vice versa. For example, for double stranded overlapping end sequences, the strands of one nucleic acid can have at least about 80%, at least about 85%, at least about 90%, at least about 95%, at least about 96%, at least about 97%, at least about 98%, at least about 99%, or 100% identity to a corresponding strand of the other nucleic acid. In methods disclosed herein, the 5' end of a strand of a dsDNA molecule to be assembled shares overlapping end sequences with the 3' end of a strand of the other dsDNA molecule. The term overlapping end sequences includes both strands of a dsDNA molecule. Thus, one strand from the overlapping region can hybridize specifically to its complementary strand when the complementary regions of the overlapping sequences are presented in single-stranded overhangs from the 5' and 3' ends of the two polynucleotides to be assembled. An exonuclease can be used to remove nucleotides from the 5' or 3' end to create overhanging end sequences.

The length of the overlapping region can be of sufficient length such that the region occurs only once within any of the nucleic acids being assembled. Thus, other polynucleotides are prevented from annealing with the end sequences, and the assembly can be specific for the target nucleic acids. As one example, the length of overlap can comprise at least about 20 nucleotides, at least about 30 nucleotides, at least about 40 nucleotides, or at least about 50 nucleotides. As another example, the length of overlap can be between about 20 nucleotides and about 100 nucleotides, between about 20 nucleotides and about 90 nucleotides, between about 0 nucleotides and about 80 nucleotides, between about 20 nucleotides and about 70 nucleotides, between about 20 nucleotides and about 60 nucleotide, between about 20 nucleotides and about 50 nucleotides, between about 20 nucleotides and about 40 nucleotides, between about 30 nucleotides and about 60 nucleotides, or between about 40 nucleotides and about 50 nucleotides. In a specific example, the length of overlap can be between about 40 nucleotides and about 50 nucleotides (e.g., about 40 nucleotides or about 50 nucleotides).

The overlapping sequences can be contacted with an exonuclease to expose complementary sequences (e.g., complementary single strand sequences) between the overlapping sequences. The exonuclease digestion can be carried out under conditions that are effective to remove (chew back) a sufficient number of nucleotides to allow for specific annealing of the exposed single-stranded regions of complementarity. In general, a portion of the region of overlap or the entire region of overlap is chewed back, leaving overhangs which comprise a portion of the region of overlap or the entire region of overlap. In some methods, the exonuclease digestion may be carried out by a polymerase in the absence of dNTPs (e.g., T5 DNA polymerase), whereas in other methods the exonuclease digestion may be carried out by an exonuclease in the presence of dNTPs that lacks polymerase activity (e.g., exonuclease III).

Any of a variety of 5'-to-3', double-strand specific exodeoxyribonucleases may be used to chew back the ends of nucleic acids in the methods disclosed herein. The term 5' exonuclease is sometimes used herein to refer to a 5'-to-3' exodeoxyribonuclease. A non-processive exonuclease refers to an exonuclease that degrades a limited number of (e.g., only a few) nucleotides during each DNA binding event. Digestion with a 5' exonuclease produces 3' single-stranded overhangs in the DNA molecules. 5' exonucleases used in in vitro assembly methods can lacks 3' exonuclease activity, can generate 5' phosphate ends, and can initiate degradation from both 5'-phosphorylated and unphosphorylated ends. Exonucleases used in the in vitro assembly methods described herein can initiate digestion from the 5' end of a molecule, whether it is a blunt end, or it has a small 5' or 3' recessed end. Suitable exonucleases are well known and include, for example, phage T5 exonuclease (phage T5 gene D15 product), phage lambda exonuclease, RecE of Rac prophage, exonuclease VIII from E. coli, phage T7 exonuclease (phage T7 gene 6 product), or any of a variety of 5' exonuclease that are involved in homologous recombination reactions. As one example, the exonuclease is T5 exonuclease or lambda exonuclease. In a specific example, the exonuclease is T5 exonuclease. In another specific example, the exonuclease is not phage T7 exonuclease.

In situations where the region of overlap is long, it may only be necessary to chew back a portion of the region, provided that the single-stranded overhangs thus generated are of sufficient length and base content to anneal specifically under the conditions of the reaction. The term annealing specifically includes situations wherein a particular pair of single-stranded overhangs will anneal preferentially (or exclusively) to one another, rather than to other single-stranded overhangs (e.g., non-complementary overhangs) that are present in the reaction mixture. By preferentially is meant that at least about 95% of the overhangs will anneal to the complementary overhang. Generally, the homologous regions of overlap (the single-stranded overhangs or their complements) contain identical sequences. However, partially identical sequences may be used, provided that the single-stranded overhangs can anneal specifically under the conditions of the reactions.

Following the annealing of single stranded DNA (e.g., overhangs produced by the action of exonuclease when the DNA molecules to be joined are dsDNA or overhangs produced by creating nicks at different target sites on each strand), the single-stranded gaps left by the exonuclease can be filled in with a suitable, non-strand-displacing, DNA polymerase and the nicks thus formed can be sealed with a ligase. A non-strand-displacing DNA polymerase as used herein is a DNA polymerase that terminates synthesis of DNA when it encounters DNA strands which lie in its path as it proceeds to copy a dsDNA molecule, or that degrades the encountered DNA strands as it proceeds while concurrently filling in the gap thus created, thereby generating a moving nick (nick translation).

Following annealing of a single strand of a first polynucleotide to the complementary strand of a second polynucleotide, the 3' end of the first polynucleotide can be extended based on the template of the second polynucleotide strand, and the 3' end of the second polynucleotide strand can be extended based on the template of the first polynucleotide strand. By extending the complementary 3' end of each polynucleotide, the polynucleotides can be assembled. Following assembly, nicks between the extended 3' end of a strand from one fragment and adjacent 5' end of a strand from the other fragment can be sealed by ligation. More specifically, the hydroxyl group of the extended 3' end of the first polynucleotide can be ligated to the phosphate group of the 5' end of the second polynucleotide, and the hydroxyl group of the extended 3' end of the second polynucleotide can be ligated to the phosphate group of the 5' end of the first polynucleotide.

The ligation reaction can be performed by any of a variety of suitable thermostable DNA ligases. Among suitable ligases are, for example, Taq ligase, Ampligase Thermostable DNA ligase, or the thermostable ligases disclosed in U.S. Pat. No. 6,576,453, herein incorporated by reference in its entirety for all purposes.

A suitable amount of a crowding agent, such as PEG, in the reaction mixture can allow for, enhance, or facilitate molecular crowding. Such a crowding agent can allow components of the solution to come into closer contact with one another. For example, DNA molecules to be recombined can come into closer proximity; which can facilitate the annealing of the single-stranded overhangs. Suitable crowding agents are known and include a variety of well-known macromolecules, such as polymers such as polyethylene glycol (PEG), Ficolls such as Ficoll 70, or dextrans such as dextran 70.

Reaction components (such as salts, buffers, a suitable energy source (such as ATP or NAD), pH of the reaction mixture, and so forth) that are present in an assembly reaction mixture may not be optimal for the individual enzymes (exonuclease, polymerase, and ligase) but can serve as a compromise that is effective for the entire set of reactions.

VI. Targeting Vectors and Large Targeting Vectors (LTVECs)

The targeting vectors used in the methods disclosed herein can be any suitable targeting vector. The targeting vectors can comprise deoxyribonucleic acid (DNA) or ribonucleic acid (RNA), they can be single-stranded or double-stranded, and they can be in linear or circular form. The targeting vectors can be a bacterial artificial chromosome (BAC), a modified BAC, or a fragment of a BAC. They can comprise human DNA, rodent DNA (e.g., mouse DNA or rat DNA), synthetic DNA, or any combination thereof.

Some targeting vectors used in the methods disclosed herein are large targeting vectors (LTVECs). LTVECs include targeting vectors that comprise homology arms that correspond to and are derived from nucleic acid sequences larger than those typically used by other approaches intended to perform homologous recombination in cells. LTVECs also include targeting vectors comprising nucleic acid inserts having nucleic acid sequences larger than those typically used by other approaches intended to perform homologous recombination in cells. For example, LTVECs make possible the modification of large loci that cannot be accommodated by traditional plasmid-based targeting vectors because of their size limitations. For example, the targeted locus can be (i.e., the 5' and 3' homology arms can correspond to) a locus of the cell that is not targetable using a conventional method or that can be targeted only incorrectly or only with significantly low efficiency in the absence of a nick or double-strand break induced by a nuclease agent (e.g., a Cas protein). Examples of LTVECs include vectors derived from a bacterial artificial chromosome (BAC), a human artificial chromosome, or a yeast artificial chromosome (YAC). Non-limiting examples of LTVECs and methods for making them are described, e.g., in U.S. Pat. Nos. 6,586,251; 6,596,541; and 7,105,348; and in WO 2002/036789, each of which is herein incorporated by reference in its entirety for all purposes. LTVECs can be in linear form or in circular form. LTVECs can be of any length and are typically at least 10 kb in length. The size of an LTVEC can be too large to enable screening of targeting events by conventional assays, e.g., southern blotting and long-range (e.g., 1 kb to 5 kb) PCR.

The targeting vectors (e.g., LTVECs) used in the methods disclosed herein can be of any length. For example, a targeting vector can be from about 10 kb to about 400 kb, from about 20 kb to about 400 kb, from about 20 kb to about 30 kb, from about 30 kb to about 40 kb, from about 40 kb to about 50 kb, from about 50 kb to about 75 kb, from about 75 kb to about 100 kb, from about 100 kb to 125 kb, from about 125 kb to about 150 kb, from about 150 kb to about 175 kb, about 175 kb to about 200 kb, from about 200 kb to about 225 kb, from about 225 kb to about 250 kb, from about 250 kb to about 275 kb or from about 275 kb to about 300 kb, from about 200 kb to about 300 kb, from about 300 kb to about 350 kb, or from about 350 kb to about 400 kb. In one example, a targeting vector can be at least about 100 kb or 100 kb in length. A targeting vector can also be from about 50 kb to about 500 kb, from about 100 kb to about 125 kb, from about 300 kb to about 325 kb, from about 325 kb to about 350 kb, from about 350 kb to about 375 kb, from about 375 kb to about 400 kb, from about 400 kb to about 425 kb, from about 425 kb to about 450 kb, from about 450 kb to about 475 kb, or from about 475 kb to about 500 kb. Alternatively, a targeting vector can be at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, at least 300 kb, at least 350 kb, at least 400 kb, at least 450 kb, or at least 500 kb or greater.

VII. Nuclease Agents

Any rare-cutting nuclease agent can be used in the methods disclosed herein. A rare-cutting nuclease agent is a nuclease agent with a target sequence or recognition sequence that occurs rarely in a genome. Similarly, any nuclease agent with a target sequence or recognition sequence that does not occur outside of the intended cleavage site(s) in the targeting vectors described herein can be used. For example, any nuclease agent that does not have a target sequence or recognition sequence in the preexisting targeting vectors in the methods described herein can be used.

Any nuclease agent as described above that induces a nick or double-strand break at a desired target sequence can be used in the methods and compositions disclosed herein. A naturally occurring or native nuclease agent can be employed so long as the nuclease agent induces a nick or double-strand break in a desired target sequence. Alternatively, a modified or engineered nuclease agent can be employed. An "engineered nuclease agent" includes a nuclease that is engineered (modified or derived) from its native form to specifically recognize and induce a nick or double-strand break in the desired target sequence. Thus, an engineered nuclease agent can be derived from a native, naturally occurring nuclease agent or it can be artificially created or synthesized. The engineered nuclease can induce a nick or double-strand break in a target sequence, for example, wherein the target sequence is not a sequence that would have been recognized by a native (non-engineered or non-modified) nuclease agent. The modification of the nuclease agent can be as little as one amino acid in a protein cleavage agent or one nucleotide in a nucleic acid cleavage agent. Producing a nick or double-strand break in a target sequence or other DNA can be referred to herein as "cutting" or "cleaving" the target sequence or other DNA.

Active variants and fragments of the exemplified target sequences are also provided. Such active variants can comprise at least 65%, 70%, 75%, 80%, 85%, 90%, 91%, 92%, 93%, 94%, 95%, 96%, 97%, 98%, 99% or more sequence identity to the given target sequence, wherein the active variants retain biological activity and hence are capable of being recognized and cleaved by a nuclease agent in a sequence-specific manner. Assays to measure the double-strand break of a target sequence by a nuclease agent are well-known. See, e.g., Frendewey et al. (2010) *Methods in Enzymology* 476:295-307, which is incorporated by reference herein in its entirety for all purposes.

Active variants and fragments of nuclease agents (i.e., an engineered nuclease agent) are also provided. Such active variants can comprise at least 65%, 70%, 75%, 80%, 85%, 90%, 91%, 92%, 93%, 94%, 95%, 96%, 97%, 98%, 99% or more sequence identity to the native nuclease agent, wherein the active variants retain the ability to cut at a desired target sequence and hence retain nick or double-strand-break-inducing activity. For example, any of the nuclease agents described herein can be modified from a native endonuclease sequence and designed to recognize and induce a nick or double-strand break at a target sequence that was not recognized by the native nuclease agent. Thus, some engineered nucleases have a specificity to induce a nick or double-strand break at a target sequence that is different from the corresponding native nuclease agent target sequence. Assays for nick or double-strand-break-inducing activity are known and generally measure the overall activity and specificity of the endonuclease on DNA substrates containing the target sequence.

A nuclease target sequence includes a DNA sequence at which a nick or double-strand break is induced by a nuclease agent. The length of the target sequence can vary, and includes, for example, target sequences that are about 30-36 bp for a zinc finger nuclease (ZFN) pair (i.e., about 15-18 bp for each ZFN), about 36 bp for a Transcription Activator-Like Effector Nuclease (TALEN), or about 20 bp for a CRISPR/Cas9 guide RNA.

A. Restriction Enzymes

Nuclease agents suitable for use in the methods disclosed herein can comprise restriction endonucleases, which include Type I, Type II, Type III, and Type IV endonucleases. Type I and Type III restriction endonucleases recognize specific recognition sites, but typically cleave at a variable position from the nuclease binding site, which can be hundreds of base pairs away from the cleavage site (recognition site). In Type II systems the restriction activity is independent of any methylase activity, and cleavage typically occurs at specific sites within or near to the binding site. Most Type II enzymes cut palindromic sequences, however Type IIa enzymes recognize non-palindromic recognition sites and cleave outside of the recognition site, Type IIb enzymes cut sequences twice with both sites outside of the recognition site, and Type IIs enzymes recognize an asymmetric recognition site and cleave on one side and at a defined distance of about 1-20 nucleotides from the recognition site. Type IV restriction enzymes target methylated DNA. Restriction enzymes are further described and classified, for example, in the REBASE database (webpage at rebase.neb.com; Roberts et al. (2003) *Nucleic Acids Res.* 31:418-20); Roberts et al. (2003) *Nucleic Acids Res.* 31:1805-12; and Belfort et al. (2002) in *Mobile DNA II*, pp. 761-783, Eds. Craigie et al. (ASM Press, Washington, D.C.), each of which is herein incorporated by reference in its entirety.

In some methods, a rare-cutting restriction enzyme is used. A rare-cutting restriction enzyme refers to an enzyme with a target site or recognition site that occurs only rarely in a genome. The size of restriction fragments generated by cutting a hypothetical random genome with a restriction enzyme may be approximated by $4^N$, where N is the number of nucleotides in the recognition site of the enzyme. For example, an enzyme with a recognition site consisting of 7 nucleotides would cut a genome once every $4^7$ bp, producing fragments of about 16,384 bp. Generally, rare-cutter enzymes have recognition sites comprising 6 or more nucleotides. For example, a rare cutter enzyme may have a recognition site comprising or consisting of 6, 7, 8, 9, 10, 11, 12, 13, 14, or 15 nucleotides. Examples of rare-cutting restriction enzymes include NotI (GCGGCCGC), XmaIII (CGGCCG), SstII (CCGCGG), SalI (GTCGAC), NruI (TCGCGA), NheI (GCTAGC), Nb.BbvCI (CCTCAGC), BbvCI (CCTCAGC), AscI (GGCGCGCC), AsiSI (GCGATCGC), FseI (GGCCGGCC), PacI (TTAATTAA), PmeI (GTTTAAAC), SbfI (CCTGCAGG), SgrAI (CRCCGGYG), SwaI (ATTTAAAT), BspQI (GCTCTTC), SapI (GCTCTTC), SfiI (GGCCNNNNNGGCC), CspCI (CAANNNNNGTGG), AbsI (CCTCGAGG), CciNI (GCGGCCGC), FspAI (RTGCGCAY), MauBI (CGCGCGCG), MreI (CGCCGGCG), MssI (GTTTAAAC), PalAI (GGCGCGCC), RgaI (GCGATCGC), RigI (GGCCGGCC), SdaI (CCTGCAGG), SfaAI (GCGATCGC), SgfI (GCGATCGC), SgrDI (CGTCGACG), SgsI (GGCGCGCC), SmiI (ATTTAAAT), SrfI (GCCCGGGC), Sse2321 (CGCCGGCG), Sse83871 (CCTGCAGG), LguI (GCTCTTC), PciSI (GCTCTTC), AarI (CACCTGC), AjuI (GAANNNNNNNTTGG), AloI (GAACNNNNNNTCC), Bad (GAAGNNNNNNTAC), PpiI (GAACNNNNNCTC), PsrI (GAACNNNNNNTAC), and others.

B. CRISPR/Cas Systems

Clustered Regularly Interspersed Short Palindromic Repeats (CRISPR)/CRISPR-associated (Cas) systems can also be used as the rare-cutting nuclease agents in the methods disclosed herein. CRISPR/Cas systems include transcripts and other elements involved in the expression of, or directing the activity of, Cas genes. A CRISPR/Cas system can be, for example, a type I, a type II, a type III system, or a type V system (e.g., subtype V-A or subtype V-B). CRISPR/Cas systems used in the compositions and methods disclosed herein can be non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, some CRISPR/Cas systems employ non-naturally occurring CRISPR complexes comprising a gRNA and a Cas protein that do not naturally occur together, employ a Cas protein that does not occur naturally, or employ a gRNA that does not occur naturally.

Cas Proteins and Polynucleotides Encoding Cas Proteins.

Cas proteins generally comprise at least one RNA recognition or binding domain that can interact with guide RNAs (gRNAs). Cas proteins can also comprise nuclease domains (e.g., DNase domains or RNase domains), DNA-binding domains, helicase domains, protein-protein interaction domains, dimerization domains, and other domains. Some such domains (e.g., DNase domains) can be from a native Cas protein. Other such domains can be added to make a modified Cas protein. A nuclease domain possesses catalytic activity for nucleic acid cleavage, which includes the breakage of the covalent bonds of a nucleic acid molecule. Cleavage can produce blunt ends or staggered ends, and it can be single-stranded or double-stranded. For example, a wild type Cas9 protein will typically create a blunt cleavage product. Alternatively, a wild type Cpf1 protein (e.g., FnCpf1) can result in a cleavage product with a 5-nucleotide 5' overhang, with the cleavage occurring after the 18th base pair from the PAM sequence on the non-targeted strand and after the 23rd base on the targeted strand. A Cas protein can have full cleavage activity to create a double-strand break at a target genomic locus (e.g., a double-strand break with blunt ends), or it can be a nickase that creates a single-strand break at a target genomic locus.

Examples of Cas proteins include Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

An exemplary Cas protein is a Cas9 protein or a protein derived from a Cas9 protein. Cas9 proteins are from a type II CRISPR/Cas system and typically share four key motifs with a conserved architecture. Motifs 1, 2, and 4 are RuvC-like motifs, and motif 3 is an HNH motif. Exemplary Cas9 proteins are from *Streptococcus pyogenes, Streptococcus thermophilus, Streptococcus* sp.*, Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp.*, Crocosphaera watsonii, Cyanothece* sp.*, Microcystis aeruginosa, Synechococcus* sp.*, Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus,*

*Pelotomaculum thermopropionicum, Acidithiobacillus caldus, Acidithiobacillus ferrooxidans, Allochromatium vinosum, Marinobacter* sp *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp *Arthrospira maxima, Arthrospira platensis, Arthrospira* sp., *Lyngbya* sp., *Microcoleus chthonoplastes, Oscillatoria* sp., *Petrotoga mobilis, Thermosipho africanus, Acaryochloris marina, Neisseria meningitidis*, or *Campylobacter jejuni*. Additional examples of the Cas9 family members are described in WO 2014/131833, herein incorporated by reference in its entirety for all purposes. Cas9 from *S. pyogenes* (SpCas9) (assigned SwissProt accession number Q99ZW2) is an exemplary Cas9 protein. Cas9 from *S. aureus* (SaCas9) (assigned UniProt accession number J7RUA5) is another exemplary Cas9 protein. Cas9 from *Campylobacter jejuni* (CjCas9) (assigned UniProt accession number Q0P897) is another exemplary Cas9 protein. See, e.g., Kim et al. (2017) *Nat. Commun.* 8:14500, herein incorporated by reference in its entirety for all purposes. SaCas9 is smaller than SpCas9, and CjCas9 is smaller than both SaCas9 and SpCas9. Cas9 from *Neisseria meningitidis* (Nme2Cas9) is another exemplary Cas9 protein. See, e.g., Edraki et al. (2019) *Mol. Cell* 73(4):714-726, herein incorporated by reference in its entirety for all purposes. Cas9 proteins from *Streptococcus thermophilus* (e.g., *Streptococcus thermophilus* LMD-9 Cas9 encoded by the CRISPR1 locus (St1Cas9) or *Streptococcus thermophilus* Cas9 from the CRISPR3 locus (St3Cas9)) are other exemplary Cas9 proteins. Cas9 from *Francisella novicida* (FnCas9) or the RHA *Francisella novicida* Cas9 variant that recognizes an alternative PAM (E1369R/E1449H/R1556A substitutions) are other exemplary Cas9 proteins. These and other exemplary Cas9 proteins are reviewed, e.g., in Cebrian-Serrano and Davies (2017) *Mamm. Genome* 28(7):247-261, herein incorporated by reference in its entirety for all purposes. An exemplary Cas9 protein sequence can comprise, consist essentially of, or consist of SEQ ID NO: 1. An exemplary DNA encoding the Cas9 protein can comprise, consist essentially of, or consist of SEQ ID NO: 2.

Another example of a Cas protein is a Cpf1 (CRISPR from *Prevotella* and *Francisella* 1) protein. Cpf1 is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in Cas9 proteins, and the RuvC-like domain is contiguous in the Cpf1 sequence, in contrast to Cas9 where it contains long inserts including the HNH domain. See, e.g., Zetsche et al. (2015) *Cell* 163(3): 759-771, herein incorporated by reference in its entirety for all purposes. Exemplary Cpf1 proteins are from *Francisella tularensis* 1, *Francisella tularensis* subsp. *novicida*, *Prevotella albensis*, *Lachnospiraceae bacterium* MC2017 1, *Butyrivibrio proteoclasticus*, *Peregrinibacteria bacterium* GW2011_GWA2_33_10, *Parcubacteria bacterium* GW2011_GWC2_44_17, *Smithella* sp. SCADC, *Acidaminococcus* sp. BV3L6, *Lachnospiraceae bacterium* MA2020, *Candidatus Methanoplasma termitum*, *Eubacterium eligens*, *Moraxella bovoculi* 237, *Leptospira inadai*, *Lachnospiraceae bacterium* ND2006, *Porphyromonas creviorican is* 3, *Prevotella disiens*, and *Porphyromonas macacae*. Cpf1 from *Francisella novicida* U112 (FnCpf1; assigned UniProt accession number A0Q7Q2) is an exemplary Cpf1 protein.

Cas proteins can be wild type proteins (i.e., those that occur in nature), modified Cas proteins (i.e., Cas protein variants), or fragments of wild type or modified Cas proteins. Cas proteins can also be active variants or fragments with respect to catalytic activity of wild type or modified Cas proteins. Active variants or fragments with respect to catalytic activity can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

Cas proteins can be modified to increase or decrease one or more of nucleic acid binding affinity, nucleic acid binding specificity, and enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity or a property of the Cas protein.

One example of a modified Cas protein is the modified SpCas9-HF1 protein, which is a high-fidelity variant of *Streptococcus pyogenes* Cas9 harboring alterations (N497A/ R661A/Q695A/Q926A) designed to reduce non-specific DNA contacts. See, e.g., Kleinstiver et al. (2016) *Nature* 529(7587):490-495, herein incorporated by reference in its entirety for all purposes. Another example of a modified Cas protein is the modified eSpCas9 variant (K848A/K1003A/ R1060A) designed to reduce off-target effects. See, e.g., Slaymaker et al. (2016) *Science* 351(6268):84-88, herein incorporated by reference in its entirety for all purposes. Other SpCas9 variants include K855A and K810A/K1003A/ R1060A. These and other modified Cas proteins are reviewed, e.g., in Cebrian-Serrano and Davies (2017) *Mamm. Genome* 28(7):247-261, herein incorporated by reference in its entirety for all purposes. Another example of a modified Cas9 protein is xCas9, which is a SpCas9 variant that can recognize an expanded range of PAM sequences. See, e.g., Hu et al. (2018) *Nature* 556:57-63, herein incorporated by reference in its entirety for all purposes.

Cas proteins can comprise at least one nuclease domain, such as a DNase domain. For example, a wild type Cpf1 protein generally comprises a RuvC-like domain that cleaves both strands of target DNA, perhaps in a dimeric configuration. Cas proteins can also comprise at least two nuclease domains, such as DNase domains. For example, a wild type Cas9 protein generally comprises a RuvC-like nuclease domain and an HNH-like nuclease domain. The RuvC and HNH domains can each cut a different strand of double-stranded DNA to make a double-stranded break in the DNA. See, e.g., Jinek et al. (2012) *Science* 337:816-821, herein incorporated by reference in its entirety for all purposes.

One or more of the nuclease domains can be deleted or mutated so that they are no longer functional or have reduced nuclease activity. For example, if one of the nuclease domains is deleted or mutated in a Cas9 protein, the resulting Cas9 protein can be referred to as a nickase and can generate a single-strand break within a double-stranded target DNA but not a double-strand break (i.e., it can cleave the complementary strand or the non-complementary strand, but not both). An example of a mutation that converts Cas9 into a nickase is a D10A (aspartate to alanine at position 10 of Cas9) mutation in the RuvC domain of Cas9 from *S. pyogenes*. Likewise, H939A (histidine to alanine at amino acid position 839), H840A (histidine to alanine at amino acid position 840), or N863A (asparagine to alanine at amino acid position N863) in the HNH domain of Cas9 from *S. pyogenes* can convert the Cas9 into a nickase. Other examples of mutations that convert Cas9 into a nickase include the corresponding mutations to Cas9 from *S. thermophilus*. See, e.g., Sapranauskas et al. (2011) *Nucleic Acids Res.* 39(21): 9275-9282 and WO 2013/141680, each of which is herein incorporated by reference in its entirety for all purposes. Such mutations can be generated using methods such as site-directed mutagenesis, PCR-mediated mutagenesis, or total gene synthesis. Examples of other mutations creating nickases can be found, for example, in WO 2013/176772 and WO 2013/142578, each of which is herein incorporated by reference in its entirety for all purposes.

Examples of inactivating mutations in the catalytic domains of xCas9 are the same as those described above for SpCas9. Examples of inactivating mutations in the catalytic domains of *Staphylococcus aureus* Cas9 proteins are also known. For example, the *Staphyloccocus aureus* Cas9 enzyme (SaCas9) may comprise a substitution at position N580 (e.g., N580A substitution) to create a nickase. Alternatively, the SaCas9 enzyme may comprise a substitution at position D10 (e.g., D10A substitution) to generate a nickase. See, e.g., WO 2016/106236, herein incorporated by reference in its entirety for all purposes. Examples of inactivating mutations in the catalytic domains of Nme2Cas9 are also known (e.g., combination of D16A and H588A). Examples of inactivating mutations in the catalytic domains of St1Cas9 are also known (e.g., combination of D9A, D598A, H599A, and N622A). Examples of inactivating mutations in the catalytic domains of St3Cas9 are also known (e.g., combination of D10A and N870A). Examples of inactivating mutations in the catalytic domains of CjCas9 are also known (e.g., combination of D8A and H559A). Examples of inactivating mutations in the catalytic domains of FnCas9 and RHA FnCas9 are also known (e.g., N995A).

Examples of inactivating mutations in the catalytic domains of Cpf1 proteins are also known. With reference to Cpf1 proteins from *Francisella novicida* U112 (FnCpf1), *Acidaminococcus* sp. BV3L6 (AsCpf1), *Lachnospiraceae bacterium* ND2006 (LbCpf1), and *Moraxella bovoculi* 237 (MbCpf1 Cpf1), such mutations can include mutations at positions 908, 993, or 1263 of AsCpf1 or corresponding positions in Cpf1 orthologs, or positions 832, 925, 947, or 1180 of LbCpf1 or corresponding positions in Cpf1 orthologs. Such mutations can include, for example one or more of mutations D908A, E993A, and D1263A of AsCpf1 or corresponding mutations in Cpf1 orthologs, or D832A, E925A, D947A, and D1180A of LbCpf1 or corresponding mutations in Cpf1 orthologs. See, e.g., US 2016/0208243, herein incorporated by reference in its entirety for all purposes.

Cas proteins can also be operably linked to heterologous polypeptides as fusion proteins. For example, a Cas protein can be fused to a cleavage domain. See WO 2014/089290, herein incorporated by reference in its entirety for all purposes. Cas proteins can also be fused to a heterologous polypeptide providing increased or decreased stability. The fused domain or heterologous polypeptide can be located at the N-terminus, the C-terminus, or internally within the Cas protein.

As one example, a Cas protein can be fused to one or more heterologous polypeptides that provide for subcellular localization. Such heterologous polypeptides can include, for example, one or more nuclear localization signals (NLS) such as the monopartite SV40 NLS and/or a bipartite alpha-importin NLS for targeting to the nucleus, a mitochondrial localization signal for targeting to the mitochondria, an ER retention signal, and the like. See, e.g., Lange et al. (2007) *J. Biol. Chem.* 282(8):5101-5105, herein incorporated by reference in its entirety for all purposes. Such subcellular localization signals can be located at the N-terminus, the C-terminus, or anywhere within the Cas protein. An NLS can comprise a stretch of basic amino acids, and can be a monopartite sequence or a bipartite sequence. Optionally, a Cas protein can comprise two or more NLSs, including an NLS (e.g., an alpha-importin NLS or a monopartite NLS) at the N-terminus and an NLS (e.g., an SV40 NLS or a bipartite NLS) at the C-terminus. A Cas protein can also comprise two or more NLSs at the N-terminus and/or two or more NLSs at the C-terminus.

Cas proteins can also be operably linked to a cell-penetrating domain or protein transduction domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, e.g., WO 2014/089290 and WO 2013/176772, each of which is herein incorporated by reference in its entirety for all purposes. The cell-penetrating domain can be located at the N-terminus, the C-terminus, or anywhere within the Cas protein.

Cas proteins provided as mRNAs can be modified for improved stability and/or immunogenicity properties. The modifications may be made to one or more nucleosides within the mRNA. Examples of chemical modifications to mRNA nucleobases include pseudouridine, 1-methylpseudouridine, and 5-methyl-cytidine. For example, capped and polyadenylated Cas mRNA containing N1-methyl pseudouridine can be used. Likewise, Cas mRNAs can be modified by depletion of uridine using synonymous codons.

Guide RNAs.

A "guide RNA" or "gRNA" is an RNA molecule that binds to a Cas protein (e.g., Cas9 protein) and targets the Cas protein to a specific location within a target DNA. Guide RNAs can comprise two segments: a "DNA-targeting segment" and a "protein-binding segment." "Segment" includes a section or region of a molecule, such as a contiguous stretch of nucleotides in an RNA. Some gRNAs, such as those for Cas9, can comprise two separate RNA molecules: an "activator-RNA" (e.g., tracrRNA) and a "targeter-RNA" (e.g., CRISPR RNA or crRNA). Other gRNAs are a single RNA molecule (single RNA polynucleotide), which can also be called a "single-molecule gRNA," a "single-guide RNA," or an "sgRNA." See, e.g., WO 2013/176772, WO 2014/065596, WO 2014/089290, WO 2014/093622, WO 2014/099750, WO 2013/142578, and WO 2014/131833, each of which is herein incorporated by reference in its entirety for all purposes. For Cas9, for example, a single-guide RNA can comprise a crRNA fused to a tracrRNA (e.g., via a linker). For Cpf1, for example, only a crRNA is needed to achieve binding to and/or cleavage of a target sequence. The terms "guide RNA" and "gRNA" include both double-molecule (i.e., modular) gRNAs and single-molecule gRNAs.

An exemplary two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA") molecule. A crRNA comprises both the DNA-targeting segment (single-stranded) of the gRNA and a stretch of nucleotides (i.e., the crRNA tail) that forms one half of the dsRNA duplex of the protein-binding segment of the gRNA. An example of a crRNA tail, located downstream (3') of the DNA-targeting segment, comprises, consists essentially of, or consists of GUUUUAGAGCUAUGCU (SEQ ID NO: 3). Any of the DNA-targeting segments disclosed herein can be joined to the 5' end of SEQ ID NO: 3 to form a crRNA.

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA. An example of a tracrRNA sequence comprises, consists essentially of, or consists of AGCAUAGCAAGUUAAAAUAAGGCUAGU-CCGUUAUCAACUUGAAAAAGUGGCACC GAGUCG-GUGCUUU (SEQ ID NO: 4). Other examples of tracrRNA sequences comprise, consist essentially of, or consist of (SEQ ID NO: 12)
AAACAGCAUAGCAAGUUAAAAUAAGGCUAGUCCGUUAUCAACUUGAAAAG UGGCACCGAGUCGGUGCUUUU
or (SEQ ID NO: 13)
GUUGGAACCAUUCAAAACAGCAUAGCAAGUUAAAAUAAGGCUAGUCCGUUA

UCAACUUGAAAAAGUGGCACCGAGUCGGUGC.

In systems in which both a crRNA and a tracrRNA are needed, the crRNA and the corresponding tracrRNA hybridize to form a gRNA. In systems in which only a crRNA is needed, the crRNA can be the gRNA. The crRNA additionally provides the single-stranded DNA-targeting segment that hybridizes to the complementary strand of a target DNA. If used for modification within a cell, the exact sequence of a given crRNA or tracrRNA molecule can be designed to be specific to the species in which the RNA molecules will be used. See, e.g., Mali et al. (2013) *Science* 339(6121):823-826; Jinek et al. (2012) *Science* 337(6096): 816-821; Hwang et al. (2013) *Nat. Biotechnol.* 31(3):227-229; Jiang et al. (2013) *Nat. Biotechnol.* 31(3):233-239; and Cong et al. (2013) *Science* 339(6121):819-823, each of which is herein incorporated by reference in its entirety for all purposes.

The DNA-targeting segment (crRNA) of a given gRNA comprises a nucleotide sequence that is complementary to a sequence on the complementary strand of the target DNA, as described in more detail below. The DNA-targeting segment of a gRNA interacts with the target DNA in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the CRISPR/Cas system and organism but often contain a targeting segment of between 21 to 72 nucleotides length, flanked by two direct repeats (DR) of a length of between 21 to 46 nucleotides (see, e.g., WO 2014/131833, herein incorporated by reference in its entirety for all purposes). In the case of *S. pyogenes*, the DRs are 36 nucleotides long and the targeting segment is 30 nucleotides long. The 3' located DR is complementary to and hybridizes with the corresponding tracrRNA, which in turn binds to the Cas protein.

The DNA-targeting segment can have, for example, a length of at least about 12, 15, 17, 18, 19, 20, 25, 30, 35, or 40 nucleotides. Such DNA-targeting segments can have, for example, a length from about 12 to about 100, from about 12 to about 80, from about 12 to about 50, from about 12 to about 40, from about 12 to about 30, from about 12 to about 25, or from about 12 to about 20 nucleotides. For example, the DNA targeting segment can be from about 15 to about 25 nucleotides (e.g., from about 17 to about 20 nucleotides, or about 17, 18, 19, or 20 nucleotides). See, e.g., US 2016/0024523, herein incorporated by reference in its entirety for all purposes. For Cas9 from *S. pyogenes*, a typical DNA-targeting segment is between 16 and 20 nucleotides in length or between 17 and 20 nucleotides in length. For Cas9 from *S. aureus*, a typical DNA-targeting segment is between 21 and 23 nucleotides in length. For Cpf1, a typical DNA-targeting segment is at least 16 nucleotides in length or at least 18 nucleotides in length.

TracrRNAs can be in any form (e.g., full-length tracrRNAs or active partial tracrRNAs) and of varying lengths. They can include primary transcripts or processed forms. For example, tracrRNAs (as part of a single-guide RNA or as a separate molecule as part of a two-molecule gRNA) may comprise, consist essentially of, or consist of all or a portion of a wild type tracrRNA sequence (e.g., about or more than about 20, 26, 32, 45, 48, 54, 63, 67, 85, or more nucleotides of a wild type tracrRNA sequence). Examples of wild type tracrRNA sequences from *S. pyogenes* include 171-nucleotide, 89-nucleotide, 75-nucleotide, and 65-nucleotide versions. See, e.g., Deltcheva et al. (2011) *Nature* 471(7340):602-607; WO 2014/093661, each of which is herein incorporated by reference in its entirety for all purposes. Examples of tracrRNAs within single-guide RNAs (sgRNAs) include the tracrRNA segments found within +48, +54, +67, and +85 versions of sgRNAs, where "+n" indicates that up to the +n nucleotide of wild type tracrRNA is included in the sgRNA. See U.S. Pat. No. 8,697,359, herein incorporated by reference in its entirety for all purposes.

The percent complementarity between the DNA-targeting segment of the guide RNA and the complementary strand of the target DNA can be at least 60% (e.g., at least 65%, at least 70%, at least 75%, at least 80%, at least 85%, at least 90%, at least 95%, at least 97%, at least 98%, at least 99%, or 100%). The percent complementarity between the DNA-targeting segment and the complementary strand of the target DNA can be at least 60% over about 20 contiguous nucleotides. As an example, the percent complementarity between the DNA-targeting segment and the complementary strand of the target DNA can be 100% over the 14 contiguous nucleotides at the 5' end of the complementary strand of the target DNA and as low as 0% over the remainder. In such a case, the DNA-targeting segment can be considered to be 14 nucleotides in length. As another example, the percent complementarity between the DNA-targeting segment and the complementary strand of the target DNA can be 100% over the seven contiguous nucleotides at the 5' end of the complementary strand of the target DNA and as low as 0% over the remainder. In such a case, the DNA-targeting segment can be considered to be 7 nucleotides in length. In some guide RNAs, at least 17 nucleotides within the DNA-targeting segment are complementary to the complementary strand of the target DNA. For example, the DNA-targeting segment can be 20 nucleotides in length and can comprise 1, 2, or 3 mismatches with the complementary strand of the target DNA. In one example, the mismatches are not adjacent to the region of the complementary strand corresponding to the protospacer adjacent motif (PAM) sequence (i.e., the reverse complement of the PAM sequence) (e.g., the mismatches are in the 5' end of the DNA-targeting segment of the guide RNA, or the mismatches are at least 2, 3, 4, 5, 6, 7, 8, 9, 10, 11, 12, 13, 14, 15, 16, 17, 18, or 19 base pairs away from the region of the complementary strand corresponding to the PAM sequence).

The protein-binding segment of a gRNA can comprise two stretches of nucleotides that are complementary to one another. The complementary nucleotides of the protein-binding segment hybridize to form a double-stranded RNA duplex (dsRNA). The protein-binding segment of a subject gRNA interacts with a Cas protein, and the gRNA directs the bound Cas protein to a specific nucleotide sequence within target DNA via the DNA-targeting segment.

Single-guide RNAs can comprise a DNA-targeting segment joined to a scaffold sequence (i.e., the protein-binding or Cas-binding sequence of the guide RNA). For example, such guide RNAs can have a 5' DNA-targeting segment and a 3' scaffold sequence. Exemplary scaffold sequences comprise, consist essentially of, or consist of: GUUUUAGAGC-UAGAAAUAGCAAGUUAAAAUAAGGCUAGUCCG-UUAUCAACUUGA AAAAGUGGCACCGAGUCGGUG-CU (version 1; SEQ ID NO: 5); GUUGGAACCAUU-CAAAACAGCAUAGCAAGUUAAAAUAAGGCUAGU-CCGUUAUCA ACUUGAAAAAGUGGCACCGAGUCG-GUGC (version 2; SEQ ID NO: 6); GUUUUAG-AGCUAGAAAUAGCAAGUUAAAAUAAGGCUAGU-CCGUUAUCAACUUGA AAAAGUGGCACCGAGUCG-GUGC (version 3; SEQ ID NO: 7); and GUUUAAGAGC-UAUGCUGGAAACAGCAUAGCAAGUUUAAAUAA-GGCUAGUCCGUUAUCAACUUGAAAAAGUGGCAC-CGAGUCGGUGC (version 4; SEQ ID NO: 8). Other exemplary scaffold sequences comprise, consist essentially of, or consist of:

```
                              (version 5; SEQ ID NO: 14)
GUUUUAGAGCUAGAAAUAGCAAGUUAAAAUAAGGCUAGUCCGUUAUCAACU

UGAAAAAGUGGCACCGAGUCGGUGCUUUUUUU;

(version 6; SEQ ID NO: 15)
GUUUUAGAGCUAGAAAUAGCAAGUUAAAAUAAGGCUAGUCCGUUAUCAACU

UGAAAAAGUGGCACCGAGUCGGUGCUUUU;
or
                              (version 7; SEQ ID NO: 16)
GUUUAAGAGCUAUGCUGGAAACAGCAUAGCAAGUUUAAAUAAGGCUAGUCC

GUUAUCAACUUGAAAAAGUGGCACCGAGUC.
```

Guide RNAs targeting any guide RNA target sequence can include, for example, a DNA-targeting segment on the 5' end of the guide RNA fused to any of the exemplary guide RNA scaffold sequences on the 3' end of the guide RNA. That is, a DNA-targeting segment can be joined to the 5' end of any one of SEQ ID NOS: 5-8 to form a single guide RNA (chimeric guide RNA). Likewise, a DNA-targeting segment can be joined to the 5' end of any one of SEQ ID NOS: 14-16 to form a single guide RNA (chimeric guide RNA). Guide RNA versions 1, 2, 3, and 4 as disclosed elsewhere herein refer to DNA-targeting segments (i.e., guide sequences or guides) joined with scaffold versions 1, 2, 3, and 4, respectively. Guide RNA versions 5, 6, and 7 as disclosed elsewhere herein refer to DNA-targeting segments (i.e., guide sequences or guides) joined with scaffold versions 5, 6, and 7, respectively.

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including DNA methyltransferases, DNA demethylases, histone acetyltransferases, histone deacetylases, and the like); and combinations thereof. Other examples of modifications include engineered stem loop duplex structures, engineered bulge regions, engineered hairpins 3' of the stem loop duplex structure, or any combination thereof. See, e.g., US 2015/0376586, herein incorporated by reference in its entirety for all purposes. A bulge can be an unpaired region of nucleotides within the duplex made up of the crRNA-like region and the minimum tracrRNA-like region. A bulge can comprise, on one side of the duplex, an unpaired 5'-XXXY-3' where X is any purine and Y can be a nucleotide that can form a wobble pair with a nucleotide on the opposite strand, and an unpaired nucleotide region on the other side of the duplex.

Unmodified nucleic acids can be prone to degradation. Exogenous nucleic acids can also induce an innate immune response. Modifications can help introduce stability and reduce immunogenicity. Guide RNAs can comprise modified nucleosides and modified nucleotides including, for example, one or more of the following: (1) alteration or replacement of one or both of the non-linking phosphate oxygens and/or of one or more of the linking phosphate oxygens in the phosphodiester backbone linkage; (2) alteration or replacement of a constituent of the ribose sugar such as alteration or replacement of the 2' hydroxyl on the ribose sugar; (3) replacement of the phosphate moiety with dephospho linkers; (4) modification or replacement of a naturally occurring nucleobase; (5) replacement or modification of the ribose-phosphate backbone; (6) modification of the 3' end or 5' end of the oligonucleotide (e.g., removal, modification or replacement of a terminal phosphate group or conjugation of a moiety); and (7) modification of the sugar. Other possible guide RNA modifications include modifications of or replacement of uracils or poly-uracil tracts. See, e.g., WO 2015/048577 and US 2016/0237455, each of which is herein incorporated by reference in its entirety for all purposes. Similar modifications can be made to Cas-encoding nucleic acids, such as Cas mRNAs.

As one example, nucleotides at the 5' or 3' end of a guide RNA can include phosphorothioate linkages (e.g., the bases can have a modified phosphate group that is a phosphorothioate group). For example, a guide RNA can include phosphorothioate linkages between the 2, 3, or 4 terminal nucleotides at the 5' or 3' end of the guide RNA. As another example, nucleotides at the 5' and/or 3' end of a guide RNA can have 2'-O-methyl modifications. For example, a guide RNA can include 2'-O-methyl modifications at the 2, 3, or 4 terminal nucleotides at the 5' and/or 3' end of the guide RNA (e.g., the 5' end). See, e.g., WO 2017/173054 A1 and Finn et al. (2018) Cell Rep. 22(9):2227-2235, each of which is herein incorporated by reference in its entirety for all purposes. In one specific example, the guide RNA comprises 2'-O-methyl analogs and 3' phosphorothioate internucleotide linkages at the first three 5' and 3' terminal RNA residues. In another specific example, the guide RNA is modified such that all 2'OH groups that do not interact with the Cas9 protein are replaced with 2'-O-methyl analogs, and the tail region of the guide RNA, which has minimal interaction with Cas9, is modified with 5' and 3' phosphorothioate internucleotide linkages. See, e.g., Yin et al. (2017) Nat. Biotech. 35(12):1179-1187, herein incorporated by reference in its entirety for all purposes. Other examples of modified guide RNAs are provided, e.g., in WO 2018/107028 A1, herein incorporated by reference in its entirety for all purposes.

gRNAs can be prepared by various other methods. For example, gRNAs can be prepared by in vitro transcription using, for example, T7 RNA polymerase (see, e.g., WO 2014/089290 and WO 2014/065596, each of which is herein incorporated by reference in its entirety for all purposes). Guide RNAs can also be a synthetically produced molecule prepared by chemical synthesis. For example, a guide RNA can be chemically synthesized to include 2'-O-methyl analogs and 3' phosphorothioate internucleotide linkages at the first three 5' and 3' terminal RNA residues.

Guide RNA Target Sequences.

Target DNAs for guide RNAs include nucleic acid sequences present in a DNA to which a DNA-targeting segment of a gRNA will bind, provided sufficient conditions for binding exist. Suitable DNA/RNA binding conditions include physiological conditions normally present in a cell. Other suitable DNA/RNA binding conditions (e.g., conditions in a cell-free system) are known in the art (see, e.g., Molecular Cloning: A Laboratory Manual, 3rd Ed. (Sambrook et al., Harbor Laboratory Press 2001), herein incorporated by reference in its entirety for all purposes). The strand of the target DNA that is complementary to and hybridizes with the gRNA can be called the "complementary strand," and the strand of the target DNA that is complementary to the "complementary strand" (and is therefore not complementary to the Cas protein or gRNA) can be called "noncomplementary strand" or "template strand."

The target DNA includes both the sequence on the complementary strand to which the guide RNA hybridizes and the corresponding sequence on the non-complementary strand (e.g., adjacent to the protospacer adjacent motif (PAM)). The term "guide RNA target sequence" as used herein refers specifically to the sequence on the non-complementary strand corresponding to (i.e., the reverse complement of) the sequence to which the guide RNA hybridizes on the complementary strand. That is, the guide RNA target sequence refers to the sequence on the non-complementary strand adjacent to the PAM (e.g., upstream or 5' of the PAM in the case of Cas9). A guide RNA target sequence is equivalent to the DNA-targeting segment of a guide RNA, but with thymines instead of uracils. As one example, a guide RNA target sequence for an SpCas9 enzyme can refer to the sequence upstream of the 5'-NGG-3' PAM on the non-complementary strand. A guide RNA is designed to have complementarity to the complementary strand of a target DNA, where hybridization between the DNA-targeting segment of the guide RNA and the complementary strand of the target DNA promotes the formation of a CRISPR complex. Full complementarity is not necessarily required, provided that there is sufficient complementarity to cause hybridization and promote formation of a CRISPR complex. If a guide RNA is referred to herein as targeting a guide RNA target sequence, what is meant is that the guide RNA hybridizes to the complementary strand sequence of the target DNA that is the reverse complement of the guide RNA target sequence on the non-complementary strand.

A target DNA or guide RNA target sequence can comprise any polynucleotide, and can be located, for example, in the nucleus or cytoplasm of a cell or within an organelle of a cell, such as a mitochondrion or chloroplast. A target DNA or guide RNA target sequence can be any nucleic acid sequence endogenous or exogenous to a cell. The guide RNA target sequence can be a sequence coding a gene product (e.g., a protein) or a non-coding sequence (e.g., a regulatory sequence) or can include both.

Site-specific binding and cleavage of a target DNA by a Cas protein can occur at locations determined by both (i) base-pairing complementarity between the guide RNA and the complementary strand of the target DNA and (ii) a short motif, called the protospacer adjacent motif (PAM), in the non-complementary strand of the target DNA. The PAM can flank the guide RNA target sequence. Optionally, the guide RNA target sequence can be flanked on the 3' end by the PAM (e.g., for Cas9). Alternatively, the guide RNA target sequence can be flanked on the 5' end by the PAM (e.g., for Cpf1). For example, the cleavage site of Cas proteins can be about 1 to about 10 or about 2 to about 5 base pairs (e.g., 3 base pairs) upstream or downstream of the PAM sequence (e.g., within the guide RNA target sequence). In the case of SpCas9, the PAM sequence (i.e., on the non-complementary strand) can be 5'-$N_1$GG-3', where $N_1$ is any DNA nucleotide, and where the PAM is immediately 3' of the guide RNA target sequence on the non-complementary strand of the target DNA. As such, the sequence corresponding to the PAM on the complementary strand (i.e., the reverse complement) would be 5'-$CCN_2$-3', where N2 is any DNA nucleotide and is immediately 5' of the sequence to which the DNA-targeting segment of the guide RNA hybridizes on the complementary strand of the target DNA. In some such cases, $N_1$ and $N_2$ can be complementary and the $N_1$-$N_2$ base pair can be any base pair (e.g., $N_1$=C and $N_2$=G; $N_1$=G and $N_2$=C; $N_1$=A and $N_2$=T; or $N_1$=T, and $N_2$=A). In the case of Cas9 from S. aureus, the PAM can be NNGRRT or NNGRR, where N can A, G, C, or T, and R can be G or A. In the case of Cas9 from C. jejuni, the PAM can be, for example, NNNNACAC or NNNNRYAC, where N can be A, G, C, or T, and R can be G or A. In some cases (e.g., for FnCpf1), the PAM sequence can be upstream of the 5' end and have the sequence 5'-TTN-3'.

An example of a guide RNA target sequence is a 20-nucleotide DNA sequence immediately preceding an NGG motif recognized by an SpCas9 protein. For example, two examples of guide RNA target sequences plus PAMs are $GN_{19}NGG$ (SEQ ID NO: 9) or $N_{20}NGG$ (SEQ ID NO: 10). See, e.g., WO 2014/165825, herein incorporated by reference in its entirety for all purposes. The guanine at the 5' end can facilitate transcription by RNA polymerase in cells. Other examples of guide RNA target sequences plus PAMs can include two guanine nucleotides at the 5' end (e.g., $GGN_{20}NGG$; SEQ ID NO: 11) to facilitate efficient transcription by T7 polymerase in vitro. See, e.g., WO 2014/065596, herein incorporated by reference in its entirety for all purposes. Other guide RNA target sequences plus PAMs can have between 4-22 nucleotides in length of SEQ ID NOS: 9-11, including the 5' G or GG and the 3' GG or NGG. Yet other guide RNA target sequences plus PAMs can have between 14 and 20 nucleotides in length of SEQ ID NOS: 9-11.

Formation of a CRISPR complex hybridized to a target DNA can result in cleavage of one or both strands of the target DNA within or near the region corresponding to the guide RNA target sequence (i.e., the guide RNA target sequence on the non-complementary strand of the target DNA and the reverse complement on the complementary strand to which the guide RNA hybridizes). For example, the cleavage site can be within the guide RNA target sequence (e.g., at a defined location relative to the PAM sequence). The "cleavage site" includes the position of a target DNA at which a Cas protein produces a single-strand break or a double-strand break. The cleavage site can be on only one strand (e.g., when a nickase is used) or on both strands of a double-stranded DNA. Cleavage sites can be at the same position on both strands (producing blunt ends; e.g. Cas9)) or can be at different sites on each strand (producing staggered ends (i.e., overhangs); e.g., Cpf1). Staggered ends can be produced, for example, by using two Cas proteins, each of which produces a single-strand break at a different cleavage site on a different strand, thereby producing a double-strand break. For example, a first nickase can create a single-strand break on the first strand of double-stranded DNA (dsDNA), and a second nickase can create a single-strand break on the second strand of dsDNA such that overhanging sequences are created. In some cases, the guide RNA target sequence or cleavage site of the nickase on the first strand is separated from the guide RNA target sequence or cleavage site of the nickase on the second strand by at least 2, 3, 4, 5, 6, 7, 8, 9, 10, 15, 20, 25, 30, 40, 50, 75, 100, 250, 500, or 1,000 base pairs.

C. Other Nuclease Agents

Any other type of known rare-cutting nuclease agent can also be used in the methods described herein. One example of such a nuclease agent is a Transcription Activator-Like Effector Nuclease (TALEN). TAL effector nucleases are a class of sequence-specific nucleases that can be used to make double-strand breaks at specific target sequences in DNA. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See WO 2010/079430; Morbitzer et al. (2010) *Proc. Natl. Acad. Sci. U.S.A.* 107(50):21617-21622; Scholze & Boch (2010) *Virulence* 1:428-432; Christian et al. *Genetics* (2010) 186:757-761; Li et al. (2010) *Nucleic Acids Res.* (2010) 39(1):359-372; and Miller et al. (2011) *Nat. Biotechnol.* 29:143-148, each of which is herein incorporated by reference in its entirety for all purposes.

Examples of suitable TAL nucleases, and methods for preparing suitable TAL nucleases, are disclosed, e.g., in US 2011/0239315, US 2011/0269234, US 2011/0145940, US 2003/0232410, US 2005/0208489, US 2005/0026157, US 2005/0064474, US 2006/0188987, and US 2006/0063231, each of which is herein incorporated by reference in its entirety for all purposes.

In some TALENs, each monomer of the TALEN comprises 33-35 TAL repeats that recognize a single base pair via two hypervariable residues. The TALEN can be a chimeric protein comprising a TAL-repeat-based DNA binding domain operably linked to an independent nuclease such as a FokI endonuclease. For example, the nuclease agent can comprise a first TAL-repeat-based DNA binding domain and a second TAL-repeat-based DNA binding domain, wherein each of the first and the second TAL-repeat-based DNA binding domains is operably linked to a FokI nuclease, wherein the first and the second TAL-repeat-based DNA binding domain recognize two contiguous target DNA sequences in each strand of the target DNA sequence separated by a spacer sequence of varying length (12-20 bp), and wherein the FokI nuclease subunits dimerize to create an active nuclease that makes a double strand break at a target sequence.

Another example of a suitable nuclease agent is a zinc-finger nuclease (ZFN). In some ZFNs, each monomer of the ZFN comprises 3 or more zinc finger-based DNA binding domains, wherein each zinc finger-based DNA binding domain binds to a 3 bp subsite. In other ZFNs, the ZFN is a chimeric protein comprising a zinc finger-based DNA binding domain operably linked to an independent nuclease such as a FokI endonuclease. For example, the nuclease agent can comprise a first ZFN and a second ZFN, wherein each of the first ZFN and the second ZFN is operably linked to a FokI nuclease subunit, wherein the first and the second ZFN recognize two contiguous target DNA sequences in each strand of the target DNA sequence separated by about 5-7 bp spacer, and wherein the FokI nuclease subunits dimerize to create an active nuclease that makes a double strand break. See, e.g., US 2006/0246567; US 2008/0182332; US 2002/0081614; US 2003/0021776; WO 2002/057308; US 2013/0123484; US 2010/0291048; WO 2011/017293; and Gaj et al. (2013) *Trends Biotechnol.*, 31(7): 397-405, each of which is herein incorporated by reference in its entirety for all purposes.

Another type of suitable nuclease agent is an engineered meganuclease. Meganucleases have been classified into four families based on conserved sequence motifs, the families are the LAGLIDADG, GIY-YIG, H—N—H, and His-Cys box families. These motifs participate in the coordination of metal ions and hydrolysis of phosphodiester bonds. Meganucleases are notable for their long target sequences, and for tolerating some sequence polymorphisms in their DNA substrates. Meganuclease domains, structure and function are known, see for example, Guhan and Muniyappa (2003) *Crit. Rev. Biochem. Mol. Biol.* 38:199-248; Lucas et al. (2001) *Nucleic Acids Res.* 29:960-9; Jurica and Stoddard, (1999) *Cell. Mol. Life Sci.* 55:1304-26; Stoddard (2006) *Q. Rev. Biophys.* 38:49-95; and Moure et al. (2002) *Nat. Struct. Biol.* 9:764, each of which is herein incorporated by reference in its entirety for all purposes. In some examples, a naturally occurring variant and/or engineered derivative meganuclease is used. Methods for modifying the kinetics, cofactor interactions, expression, optimal conditions, and/or target sequence specificity, and screening for activity are known. See, e.g., Epinat et al. (2003) *Nucleic Acids Res.* 31:2952-62; Chevalier et al. (2002) *Mol. Cell* 10:895-905; Gimble et al. (2003) *Mol. Biol.* 334:993-1008; Seligman et al. (2002) *Nucleic Acids Res.* 30:3870-9; Sussman et al. (2004) *J. Mol. Biol.* 342:31-41; Rosen et al. (2006) *Nucleic Acids Res.* 34:4791-800; Chames et al. (2005) *Nucleic Acids Res.* 33:e178; Smith et al. (2006) *Nucleic Acids Res.* 34:e149; Gruen et al. (2002) *Nucleic Acids Res.* 30:e29; Chen and Zhao (2005) *Nucleic Acids Res.* 33:e154; WO 2005/105989; WO 2003/078619; WO 2006/097854; WO 2006/097853; WO 2006/097784; and WO 2004/031346, each of which is herein incorporated by reference in its entirety for all purposes.

Any meganuclease can be used, including, for example, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NcIIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any active variants or fragments thereof.

Meganucleases can recognize, for example, double-stranded DNA sequences of 12 to 40 base pairs. In some cases, the meganuclease recognizes one perfectly matched target sequence in the genome. Some meganucleases are homing nucleases. One type of homing nuclease is a LAGLIDADG family of homing nucleases including, for example, I-SceI, I-CreI, and I-DmoI.

VIII. Selection Cassettes

Any suitable selection cassette can be used in the methods described herein. The term selection cassette refers to an expression cassette that comprises one or more expression control sequences (e.g. a promoter for expression in a bacterial cell and/or other regulatory sequences such as enhancers, post-transcriptional regulatory elements, and poly(A) sequences) operably linked to a nucleic acid encoding a selectable marker. Selection cassettes can allow for selection in bacterial cells, or they can allow for selection in both bacterial and eukaryotic or mammalian cells. As one example, a gene such as neomycin phosphotransferase can be used. Neomycin phosphotransferase confers kanamycin resistance in prokaryotic cells and G418 resistance in eukaryotic cells. Such a gene can be used, for example, in combination with a dual promoter system combining a eukaryotic promoter (e.g., a eukaryotic phosphoglycerate kinase (PGK) promoter) and a prokaryotic promoter (e.g., a prokaryotic EM7 promoter).

Some selection cassettes that can be used in the methods described herein can impart resistance to an antibiotic that would otherwise kill or inhibit the growth of the bacterial cells. For example, a selection cassette can impart resistance to kanamycin, spectinomyin, streptomycin, ampicillin, carbenicillin, bleomycin, erythromycin, polymxin B, tetracycline, or chloramphenicol. Such selection cassettes and genes that impart resistance to these antibiotics and others are well-known. Cells comprising the selection cassettes can be selected by treating the cells with the antibiotic. Those cells that are resistant to the antibiotic comprise the selection cassette.

Other selection cassettes can comprise reporter genes that can be used to select for cells comprising an intended modification. The term reporter gene refers to a nucleic acid having a sequence encoding a gene product (typically an enzyme) that is easily and quantifiably assayed when a construct comprising the reporter gene sequence operably linked to a heterologous promoter and/or enhancer element is introduced into cells containing (or which can be made to contain) the factors necessary for the activation of the promoter and/or enhancer elements. Examples of reporter genes include, but are not limited, to genes encoding fluorescent proteins. A reporter protein refers to a protein encoded by a reporter gene.

A fluorescent reporter protein is a reporter protein that is detectable based on fluorescence wherein the fluorescence may be either from the reporter protein directly, activity of the reporter protein on a fluorogenic substrate, or a protein with affinity for binding to a fluorescent tagged compound. Examples of fluorescent proteins include green fluorescent proteins (e.g., GFP, GFP-2, tagGFP, turboGFP, eGFP, Emerald, Azami Green, Monomeric Azami Green, CopGFP, AceGFP, and ZsGreenl), yellow fluorescent proteins (e.g., YFP, eYFP, Citrine, Venus, YPet, PhiYFP, and ZsYellowl), blue fluorescent proteins (e.g., BFP, eBFP, eBFP2, Azurite, mKalamal, GFPuv, Sapphire, and T-sapphire), cyan fluorescent proteins (e.g., CFP, eCFP, Cerulean, CyPet, AmCyanl, and Midoriishi-Cyan), red fluorescent proteins (e.g., RFP, mKate, mKate2, mPlum, DsRed monomer, mCherry, mRFP1, DsRed-Express, DsRed2, DsRed-Monomer, HcRed-Tandem, HcRedl, AsRed2, eqFP611, mRaspberry, mStrawberry, and Jred), orange fluorescent proteins (e.g., mOrange, mKO, Kusabira-Orange, Monomeric Kusabira-Orange, mTangerine, and tdTomato), and any other suitable fluorescent protein whose presence in cells can be detected by flow cytometry methods. Cells comprising a fluorescent reporter gene can be selected, for example, by sorting for cells comprising the fluorescent reporter protein encoded by the gene.

IX. Targeted Modifications

Various types of targeted genetic modifications can be introduced using the methods described herein. Such targeted genetic modifications can include, for example, insertion of one or more nucleotides, deletion of one or more nucleotides, or substitution (replacement) of one or more nucleotides. Such insertions, deletions, or replacements can result, for example, in a point mutation, a knockout of a nucleic acid sequence of interest or a portion thereof, a knock-in of a nucleic acid sequence of interest or a portion thereof, a replacement of an endogenous nucleic acid sequence with a heterologous or exogenous nucleic acid sequence, a replacement of an endogenous nucleic acid sequence with a homologous or orthologous nucleic acid sequence (e.g., domain swap, exon swap, intron swap, regulatory sequence swap, or gene swap), alteration of a regulatory element (e.g., promoter or enhancer), a missense mutation, a nonsense mutation, a frame-shift mutation, a truncation mutation, a null mutation, or a combination thereof. For example, at least 1, 2, 3, 4, 5, 7, 8, 9, 10 or more nucleotides can be changed (e.g., deleted, inserted, or substituted) to form the targeted genetic modification. The deletions, insertions, or replacements can be of any size, as disclosed elsewhere herein. See, e.g., Wang et al. (2013) Cell 153:910-918; Mandalos et al. (2012) PLOS One 7:e45768; and Wang et al. (2013) Nat Biotechnol. 31:530-532, each of which is herein incorporated by reference in its entirety.

Deletions, insertions, or replacements can be any length. The deleted, inserted, or replaced nucleic acid can be, for example, from about 1 bp to about 5 bp, from about 5 bp to about 10 bp, from about 10 bp to about 50 bp, from about 50 bp to about 100 bp, from about 100 bp to about 200 bp, from about 200 bp to about 300 bp, from about 300 bp to about 400 bp, from about 400 bp to about 500 bp, from about 500 bp to about 1 kb, from about 1 kb to about 5 kb, from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, or from about 400 kb to about 500 kb.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. When a nucleotide sequence encoding an amino acid sequence is provided, it is understood that codon degenerate variants thereof that encode the same amino acid sequence are also provided. The amino acid sequences follow the standard convention of beginning at the amino terminus of the sequence and proceeding forward (i.e., from left to right in each line) to the carboxy terminus.

TABLE 2

Description of Sequences.

| SEQ ID NO | Type | Description |
|---|---|---|
| 1 | Protein | Cas9 Protein |
| 2 | DNA | Cas9 DNA |
| 3 | RNA | crRNA tail |
| 4 | RNA | tracrRNA |
| 5 | RNA | gRNA scaffold v1 |
| 6 | RNA | gRNA scaffold v2 |
| 7 | RNA | gRNA scaffold v3 |
| 8 | RNA | gRNA scaffold v4 |
| 9 | DNA | guide RNA target sequence plus PAM v1 |
| 10 | DNA | guide RNA target sequence plus PAM v2 |
| 11 | DNA | guide RNA target sequence plus PAM v3 |
| 12 | RNA | tracrRNA v2 |
| 13 | RNA | tracrRNA v3 |
| 14 | RNA | gRNA scaffold v5 |
| 15 | RNA | gRNA scaffold v6 |
| 16 | RNA | gRNA scaffold v7 |

EXAMPLES

Example 1. Scarless Introduction of a Targeted Modification into a Large Targeting Vector Via Bacterial Homologous Recombination and Intramolecular Gibson Assembly Gibson assembly technology joins segments of DNA with homologous ends into a single molecule. It differs from traditional ligations between complementary, staggered ends created by restriction enzymes in that any complementary sequence of a minimal size can be used. As cloning via restriction sites generally results in incorporation of exogenous DNA scars (enzyme recognition sites) into the final product, Gibson assembly is advantageous because it can be seamless.

The Gibson assembly reaction is isothermal and involves three different enzymes: T5 exonuclease, DNA polymerase, and ligase. See, e.g., US 2010/0035768, US 2015/0376628, WO 2015/200334, and Gibson et al. (2009) Nat. Methods 6(5):343-345, each of which is herein incorporated by reference in its entirety for al purposes. The reaction begins with the generation of single-stranded DNA ends due to 5' to 3' exonuclease activity by the T5 exonuclease. DNA fragments with complementary single-stranded ends then align by simple base-pairing rules, and DNA polymerase fills gaps moving 5' to 3'. DNA ligase seals the final nick and a seamless, double-stranded DNA molecule is the result. Complementary ends of forty base pairs have been shown to be effective, and the actual sequence is generally not important. The starting fragments can be generated by PCR, restriction, or direct synthesis.

Seamless DNA construction is of particular importance when creating transgenic animal lines, as the scars produced by restriction sites or other manipulations can negatively impact gene expression if they land in a region important for regulation. Targeting the mammalian genome often requires construction of large targeting vectors with long DNA arms to direct homologous recombination, as well as antibiotic resistance cassettes for selection of embryonic stem cell clones. Correctly targeted clones often contain multiple scars necessary for construction of the vector, not to mention the resistance cassette itself. For genetic ablation, these lesions may not matter for the end result (a null allele), but there is always the chance that expression by neighboring genes will be adversely affected. For modifications other than knock-out, such as knock-in (e.g., reporters or mutant alleles), faithful expression of the targeted locus is usually important for the studies in question. Gibson assembly can abrogate the need for some of these scars and even facilitate construction of the vector itself in some cases, but unique restriction sites can be difficult to find.

Humanization, the direct replacement of a mouse gene with its human counterpart, in particular requires seamless junctions between mouse and human sequence so that mouse transcription machinery will faithfully replicate expression of the new allele. Care must be taken to bury construction scars and selection cassette in noncoding regions that do not impact gene regulation. As animal models become more complex, more modifications may be added on top of existing ones, such as human disease-causing mutations on humanized alleles. The additional changes can then add even more scars and another selection cassette to an already highly engineered mouse locus, increasing the likelihood that expression will be altered and the mouse model will not be faithful to human disease. From a construction standpoint, adding a new cassette to a vector already containing one can become complicated due to undesired recombination between shared cassette elements such as promoters and poly(A) signals, even if the two cassettes encode different selections.

In view of these hurdles, we have developed methods to simplify generating targeting vectors carrying multiple changes such as a humanized allele and a disease mutation layered on top. These methods enable easier construction and minimize scars incorporated into the final animal model.

In a first method, a small piece of DNA carrying a desired mutation is synthesized flanked by short (<500 bp) homology arms. A few base pairs downstream of the desired mutation, a 40-50 base pair region is selected and duplicated to create direct repeats to flank rare restriction sites or Cas9 guide RNA target sequences flanking a resistance cassette. This small construct is then homologously recombined with an established mouse targeting vector (such as a humanization targeting vector, with its own resistance cassette) by recombineering technology. After confirmation that the desired mutation is incorporated, the new vector is cut with the rare cutter/Cas9 guide, dropping out the cassette and exposing the 40-50 base pair direct repeats. Gibson assembly then seals the break seamlessly in an intramolecular reaction. The resulting targeting vector now carries the desired mutation and no additional scars or cassette besides the ones originally present in the humanization.

Figure 2:
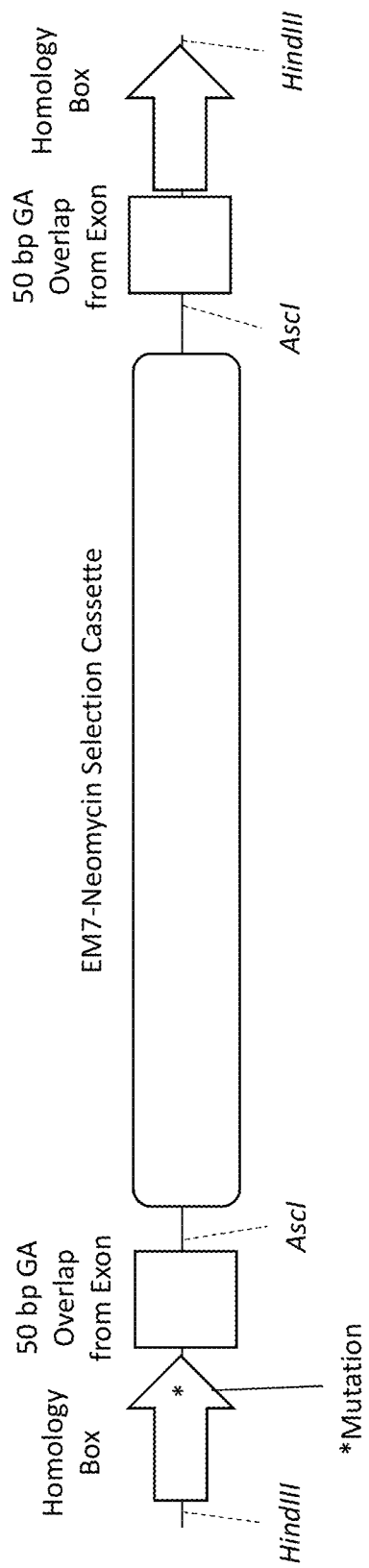
FIG. 2 (not to scale) shows a schematic of a synthesized nucleic acid to be used in the method shown in the schematic in FIG. 1.

In a specific example, we generated an allele incorporating a point mutation into a targeting construct (a large targeting vector) comprising a humanized Target Gene 1. See FIG. 1. The goal was to efficiently and seamlessly create a large targeting vector comprising a humanized Target Gene 1 with the point mutation instead of having to retarget humanized mouse embryonic stem (ES) cells comprising the humanized Target Gene 1 in order to introduce the point mutation in those humanized mouse ES cells. The initial targeting construct contained the human Target Gene 1 genomic sequence from the start codon to the stop codon, including all introns, to replace the mouse genomic sequence of the corresponding mouse Target Gene 1 from the start codon to the stop codon. In addition, the insert nucleic acid in the targeting construct comprised a self-deleting hygromycin resistance cassette downstream of the poly(A) sequence. This starting humanization vector was then modified as described above with the point mutation and a neomycin resistance cassette, flanked by AscI restriction sites and 50 base pair direct repeats of human Target Gene 1 sequence just downstream of the point mutation. A nucleic acid was then synthesized to comprise an EM7 neomycin cassette flanked by rare restriction sites (AscI) and a 50 bp direct repeat from the exon into which the mutation was to be introduced as well as upstream and downstream homology boxes, including the mutation to be introduced in the upstream homology box. See FIG. 2. The neomycin resistant cassette was inserted into the middle of the exon to be mutated, but because the method is seamless, the exon was recapitulated at the end of the method. The nucleic acid was linearized by cleavage with HindIII, and bacterial homologous recombination was used to insert the linearized synthetic nucleic acid into the large targeting vector comprising the humanized Target Gene 1. See, e.g., US 2004/0018626 and Valenzuela et al. (2003) Nat. Biotechnol. 21(6):652-659, each of which is herein incorporated by reference in its entirety. The neomycin cassette was excised with AscI, which dropped out the neomycin cassette and exposed the direct repeats. The construct was then resealed by intramolecular Gibson assembly, which resolved the direct repeats to a single copy, leaving the exon (now comprising the mutation) intact with no scars. Following Gibson assembly, the reaction was again digested with AscI, in order to cut anything that did not delete the AscI sites during Gibson assembly, thereby reducing background. Final sequencing confirmed the presence of the point mutation and no additional changes from the original targeting vector. The newly modified vector was electroporated into mouse embryonic stem cells, and positive clones were identified by TAQMAN followed by Sanger sequencing to confirm the incorporation of the point mutation.

Figure 3:
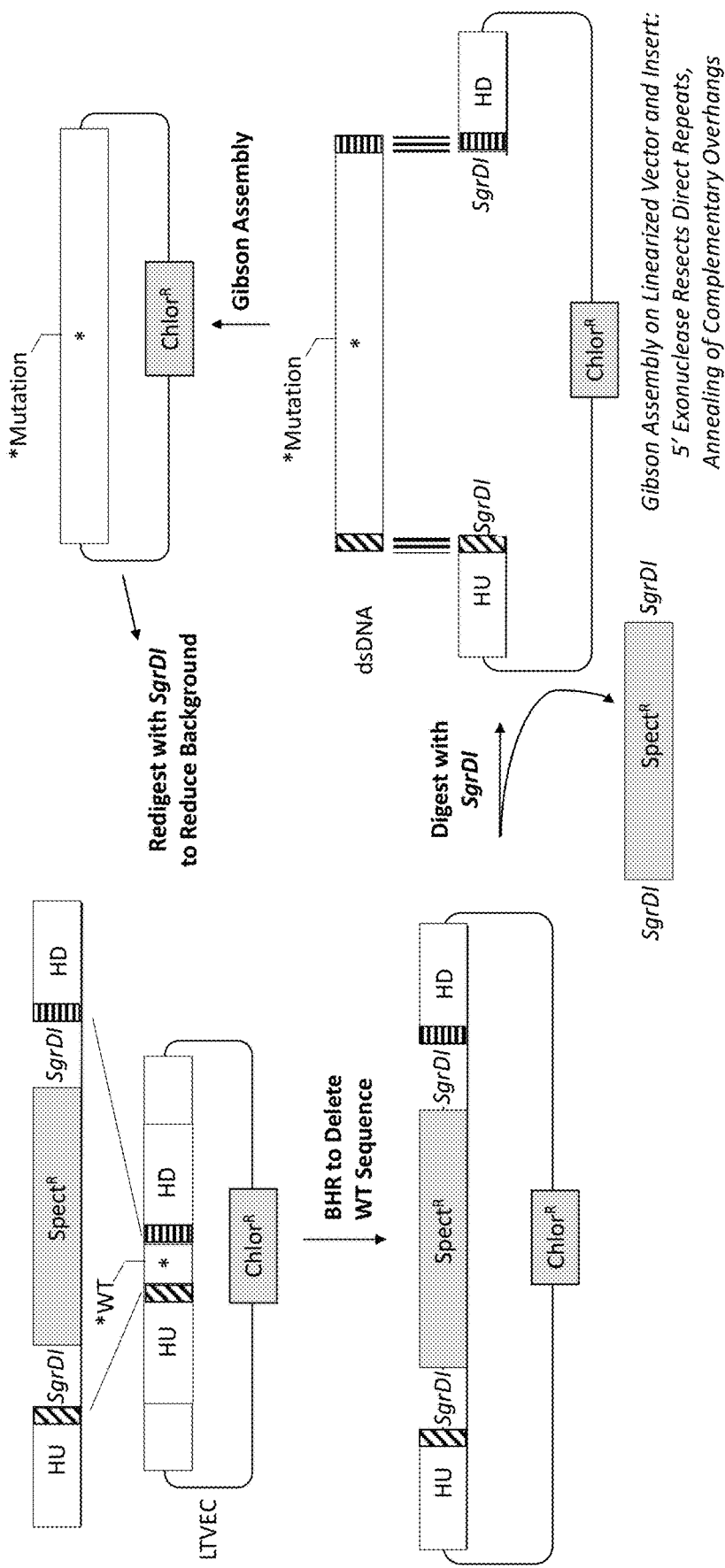
FIG. 3 (not to scale) shows a schematic of a method for scarless introduction of a point mutation into a large targeting vector via bacterial homologous recombination and intermolecular Gibson assembly.

Example 2. Scarless Introduction of a Targeted Modification into a Large Targeting Vector Via Bacterial Homologous Recombination and Intermolecular Gibson Assembly In a second method, a desired mutation is introduced into a bacterial artificial chromosome (BAC) DNA in two general steps. In the first step, the region of interest in the BAC (a region spanning about 100-200 bp on each side of the mutation) is deleted by bacterial homologous recombination using a selection cassette flanked by a rare cutter restriction enzyme site on each side. In the second step, the BAC deletion s replaced with the desired mutated sequence by Gibson assembly using a DNA fragment of about 200-500 bp having heterologous 5' and 3' ends homologous to the targeted BAC sequence adjacent to the rare cutter site. For this purpose, the targeted BAC in the first step is digested with the rare cutter enzyme, exposing the two ends homologous to the mutated fragment. The restriction enzyme also keeps the targeted BAC open, allowing for a low background reaction without the need to add a selection marker. See FIG. 3. This method is particularly beneficial, for example, when larger fragments that cannot be obtained by PCR (e.g., 15 kb or 30 kb) need to be inserted in a construct. For example, such a large fragment can be cut from its source like a BAC (e.g., using CRISPR/Cas9), and then inserted using Gibson assembly a modified BAC that carries homology to the 5' and 3' ends of this fragment, thereby creating the final targeting construct.

In a specific example, this method was used to introduce a splice mutation into a large targeting vector comprising a humanized Target Gene 2. The initial targeting construct contained the wild type Target Gene 2 genomic sequence, including introns, designed to replace the corresponding genomic sequence of the mouse Target Gene 2 from the start codon to before last exon, including adding a self-deleting neomycin resistance cassette in an intron. This starting humanization vector was then modified as described above with a hygromycin resistance cassette, flanked by AscI restriction sites and forty base pairs homologous sequence to downstream and upstream of the desired splice mutation. The hygromycin cassette was excised with AscI, and the construct was resealed by intermolecular Gibson assembly with a DNA fragment comprising the splice mutation flanked by heterologous 5' and 3' ends homologous to the targeted targeting construct sequence adjacent to the rare cutter site. Final sequencing confirmed the presence of the splice mutation and no additional changes from the original targeting vector. The newly modified vector was electroporated into mouse embryonic stem cells and a positive clone was identified by TAQMAN, followed by Sanger sequencing to confirm the incorporation of the splice mutation.

In a third method, a human DNA fragment from a bacterial artificial chromosome (BAC) is cut out using CRISPR/Cas9. This human DNA fragment is fused, by Gibson assembly, to a mouse BAC that was previously targeted with a selection cassette. A rare cutter restriction enzyme site is designed in region where the human fragment was to be integrated. In the targeted mouse BAC, there are 40 bp of homology sequences on each side of this rare cutter restriction site. The homology sequences are homologous to the 5' and 3' ends of the human DNA fragment. The final construct is selected in the same antibiotic as the original mouse BAC targeted. Even though no new selection is incorporated in the final Gibson assembly reaction, low background is observed. Addition of the rare restriction enzyme following Gibson assembly keeps the background at low level.

In a specific example, the above experiment was to incorporate an allele comprising the region of Target Gene 3 encoding the ectodomain of Target Protein 3 into the mouse Target Gene 3. The initial targeting construct contained the wild type mouse Target Gene 3 genomic sequence, including introns. A self-deleting neomycin resistance cassette was added by bacterial homologous recombination, deleting the mouse Target Gene 3 ectodomain-encoding region. Upstream the neomycin resistance cassette, there was a SgrDI restriction site that separates the 5' and 3' 40 bp regions of human homology that will interact with the human fragment. All of these sequences were incorporated by bacterial homologous recombination previously described. A human DNA fragment 32 kb in length was excised from a human BAC by CRISPR/Cas9, leaving the 5' and 3' ends exposed for the intramolecular Gibson assembly reaction with the mouse targeted BAC that was opened by SgrDI digestion. The newly modified vector was electroporated into mouse embryonic stem cells, and a positive clone was identified by TAQMAN.

We claim:

1. A method for introducing a scarless targeted genetic modification in a preexisting targeting vector, comprising:
   (a) performing bacterial homologous recombination between the preexisting targeting vector and a modification cassette in a population of bacterial cells, wherein the modification cassette comprises the targeted genetic modification and comprises an insert nucleic acid flanked by a 5' homology arm corresponding to a 5' target sequence in the preexisting targeting vector and a 3' homology arm corresponding to a 3' target sequence in the preexisting targeting vector, wherein the insert nucleic acid comprises from 5' to 3':
      (i) a first repeat sequence;
      (ii) a first target site for a first nuclease agent;
      (iii) a selection cassette;
      (iv) a second target site for a second nuclease agent; and
      (v) a second repeat sequence identical to the first repeat sequence,
      wherein the repeat sequence is at least about 20 nucleotides in length;
   (b) selecting bacterial cells comprising a modified targeting vector comprising the selection cassette;
   (c) cleaving the first target site in the modified targeting vector with the first nuclease agent and cleaving the second target site in the modified targeting vector with the second nuclease agent to remove the selection cassette and expose the first repeat sequence and the second repeat sequence in the modified targeting vector,
   wherein step (c) occurs in vitro; and
   (d) assembling the exposed first repeat sequence with the exposed second repeat sequence in an intramolecular in vitro assembly reaction to generate the targeting vector comprising the scarless targeted genetic modification, wherein neither the first target site for the first nuclease agent nor the second target site for the second nuclease agent are present and only a single copy of the repeat sequence is present in the targeting vector comprising the scarless targeted genetic modification.

2. The method of claim 1, wherein the repeat sequence is identical to a sequence in the preexisting targeting vector.

3. The method of claim 1, wherein the targeted genetic modification comprises an insertion, and the repeat sequence is identical to the 5' end or the 3' end of the insertion.

4. The method of claim 1, wherein the repeat sequence is between about 20 nucleotides and about 100 nucleotides in length.

5. The method of claim 1, wherein the modification cassette is a linear, double-stranded nucleic acid.

6. The method of claim 1, wherein the modification cassette is from about 1 kb to about 15 kb in length.

7. The method of claim 1, wherein the 5' homology arm and the 3' homology arm are each at least about 35 nucleotides in length.

8. The method of claim 7, wherein the 5' homology arm and the 3' homology arm are each between about 35 nucleotides and about 500 nucleotides in length.

9. The method of claim 1, wherein the first nuclease agent and/or the second nuclease agent is a rare-cutting nuclease agent.

10. The method of claim 1, wherein the first target site and/or the second target site is not present in the preexisting targeting vector.

11. The method of claim 1, wherein the first target site is identical to the second target site, and the first nuclease agent is identical to the second nuclease agent.

12. The method of claim 1, wherein the first nuclease agent and/or the second nuclease agent comprises a rare-cutting restriction enzyme.

13. The method of claim 12, wherein the rare-cutting restriction enzyme is NotI, XmaIII, SstII, SalI, NruI, NheI, Nb.BbvCI, BbvCI, AscI, AsiSI, FseI, PacI, PmeI, SbfI, SgrAI, SwaI, BspQI, SapI, SfiI, CspCI, AbsI, CciNI, FspAI, MauBI, MreI, MssI, PalAI, RgaI, RigI, SdaI, SfaAI, SgfI, SgrDI, SgsI, SmiI, SrfI, Sse2321, Sse83871, LguI, PciSI, AarI, AjuI, AloI, BarI, PpiI, or PsrI.

14. The method of claim 1, wherein the first nuclease agent and/or the second nuclease agent is a Clustered Regularly Interspaced Short Palindromic Repeats (CRISPR)-associated (Cas) protein and a guide RNA (gRNA), a zinc finger nuclease (ZFN), a Transcription Activator-Like Effector Nuclease (TALEN), or an engineered meganuclease.

15. The method of claim 14, wherein the first nuclease agent and/or the second nuclease agent is the Cas protein and the gRNA, wherein the Cas protein is Cas9, and wherein the gRNA comprises a CRLSPR RNA (crRNA) and a trans-activating CRISPR RNA (tracrRNA).

16. The method of claim 1, wherein the targeted genetic modification comprises a modification in the 5' homology arm or the 3' homology arm.

17. The method of claim 1, wherein the targeted genetic modification comprises a modification in the insert nucleic acid.

18. The method of claim 1, wherein the targeted genetic modification comprises a point mutation, a deletion, an insertion, a replacement, or a combination thereof.

19. The method of claim 1, wherein the selection cassette imparts resistance to an antibiotic.

20. The method of claim 19, wherein the selection cassette imparts resistance to ampicillin, chloramphenicol, tetracycline, kanamycin, spectinomycin, streptomycin, carbenicillin, bleomycin, erythromycin, or polymyxin B.

21. The method of claim 1, wherein the preexisting targeting vector is a large targeting vector at least about 10 kb in length.

22. The method of claim 21, wherein the preexisting targeting vector is at least about 100 kb in length.

23. The method of claim 1, wherein the preexisting targeting vector comprises a second selection cassette.

24. The method of claim 23, wherein the second selection cassette imparts resistance to an antibiotic.

25. The method of claim 24, wherein the selection cassette in the modification cassette and the second selection cassette in the preexisting targeting vector each impart resistance to a different antibiotic.

26. The method of claim 23, wherein the second selection cassette allows for selection in both bacterial and mammalian cells.

27. The method of claim 1, wherein step (d) comprises:
(i) contacting the modified targeting vector with an exonuclease to expose complementary sequences between the first repeat sequence and the second repeat sequence;
(ii) annealing the exposed complementary sequences;
(iii) extending the 3' ends of the annealed complementary sequences; and
(iv) ligating the annealed complementary sequences.

28. The method of claim 27, wherein step (d) comprises incubating the modified targeting vector with an exonuclease, a DNA polymerase, and a DNA ligase.

29. The method of claim 1, further comprising:
(e) treating the targeting vector with the first nuclease agent and the second nuclease agent following the in vitro assembly in step (d) to verify that neither the first target site for the first nuclease agent nor the second target site for the second nuclease agent are present.

* * * * *

UNITED STATES PATENT AND TRADEMARK OFFICE
CERTIFICATE OF CORRECTION

PATENT NO. : 11,111,504 B2  
APPLICATION NO. : 16/838621  
DATED : September 7, 2021  
INVENTOR(S) : Susannah Brydges et al.

Page 1 of 1

It is certified that error appears in the above-identified patent and that said Letters Patent is hereby corrected as shown below:

In the Claims

Column 66, Claim 15, Line 53: delete "CRLSPR" and insert --CRISPR--

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*